(12) United States Patent
Kaneda

(10) Patent No.: US 11,041,006 B2
(45) Date of Patent: Jun. 22, 2021

(54) COMPOSITIONS FOR USE IN RECOVERING OR AMELIORATING DETERIORATION OF PHYSIOLOGICAL FUNCTIONS DUE TO AGING

(71) Applicant: RIKEN, Wako (JP)

(72) Inventor: Hayato Kaneda, Wako (JP)

(73) Assignee: RIKEN, Wako (JP)

( * ) Notice: Subject to any disclaimer, the term of this patent is extended or adjusted under 35 U.S.C. 154(b) by 123 days.

(21) Appl. No.: 15/777,019

(22) PCT Filed: Dec. 27, 2016

(86) PCT No.: PCT/JP2016/088865
§ 371 (c)(1),
(2) Date: May 17, 2018

(87) PCT Pub. No.: WO2017/115789
PCT Pub. Date: Jul. 6, 2017

(65) Prior Publication Data
US 2018/0334487 A1 Nov. 22, 2018

(30) Foreign Application Priority Data

Dec. 28, 2015 (JP) .............................. JP2015-256045

(51) Int. Cl.
| | |
|---|---|
| *C07K 14/495* | (2006.01) |
| *A61P 43/00* | (2006.01) |
| *C12N 15/113* | (2010.01) |
| *A61K 31/7105* | (2006.01) |
| *A61K 35/28* | (2015.01) |
| *A61K 35/76* | (2015.01) |
| *C12N 5/0775* | (2010.01) |
| *A61K 38/18* | (2006.01) |
| *A61K 48/00* | (2006.01) |
| *A61K 38/00* | (2006.01) |

(52) U.S. Cl.
CPC ........ *C07K 14/495* (2013.01); *A61K 31/7105* (2013.01); *A61K 35/28* (2013.01); *A61K 35/76* (2013.01); *A61K 38/1841* (2013.01); *A61K 48/00* (2013.01); *A61P 43/00* (2018.01); *C12N 5/0668* (2013.01); *C12N 15/113* (2013.01); *A01K 2207/12* (2013.01); *A01K 2217/052* (2013.01); *A01K 2227/105* (2013.01); *A01K 2267/035* (2013.01); *A61K 38/00* (2013.01); *A61K 48/005* (2013.01); *C12N 2310/141* (2013.01); *C12N 2501/15* (2013.01); *C12N 2740/16043* (2013.01)

(58) Field of Classification Search
None
See application file for complete search history.

(56) References Cited

U.S. PATENT DOCUMENTS

| | | | |
|---|---|---|---|
| 8,828,941 B2 * | 9/2014 | Diwan ................. | A61K 9/0085 |
| | | | 514/17.1 |
| 9,845,465 B2 * | 12/2017 | Annex ................. | C12N 15/113 |
| 10,322,166 B2 * | 6/2019 | Diwan ............... | A61K 38/1709 |
| 2011/0144718 A1 | 6/2011 | Diwan et al. | |
| 2015/0037229 A1 | 2/2015 | Bell et al. | |
| 2015/0104870 A1 | 4/2015 | Kaneda et al. | |

FOREIGN PATENT DOCUMENTS

| | | |
|---|---|---|
| JP | 2008-519606 A | 6/2008 |
| JP | 2015-509366 A | 3/2015 |
| WO | WO-2006/137941 A2 | 12/2006 |
| WO | WO-2013/142114 A1 | 9/2013 |
| WO | WO-2013/162027 A1 | 10/2013 |

OTHER PUBLICATIONS

Wolfman (1997) "Ectopic Induction of Tendon and Ligament in Rats by Growth and Differentiation Factors 5, 6, and 7, Members of the TGF-β Gene Family", Journal of Clinical Investigation, 100(2): 321-330. (Year: 1997).*
Hanel, et al. (2006) "Eye and neural defects associated with loss of GDF6", BMC Developmental Biology, 4: article 43 (13 pages long). (Year: 2006).*
Mi, et al. (2010) "Aberrant overexpression and function of the miR-17-92 cluster in MLL-rearranged acute leukemia", Proceedings of the National Academy of Science, USA., 107(8): 3710-15. (Year: 2010).*
Hisamatsu, et al. (2016) "Reversing multiple age-related pathologies by controlling the senescence-associated secretory phenotype of stem cells", Neural Regeneration Research, 11(11): 1746-47.*
Bhat, et al. (2012) "Astrocyte Senescence as a Component of Alzheimer's Disease", PLoS one, 7(9): article e45069, 10 pages. (Year: 2012).*
Barberi, et al. (2015) "Molecular and Cellular Mechanisms of Muscle Aging and Sarcopenia and Effects of Electrical Stimulation in Seniors", European Journal of Translational Myology, 25(4): 231-36. (Year: 2015).*
Jia & Nash (2015) "Pathology of Aging Skin", Textbook of Aging Skin, Published By Springer Link, Berlin, DE, Farange, Miller and Maibach (eds), pp. 1-23. (Year: 2015).*
Hodgkinson, et al. (2019) Microparticles for controlled GDF6 delivery to direct ASC-based nucleus pulposus regeneration, Journal of Tissue Engineering and Regenerative Medicine, 13(8): Article DOI: 10.1002/term.2882, 25 pages. (Year: 2019).*

(Continued)

*Primary Examiner* — Robert M Kelly
(74) *Attorney, Agent, or Firm* — Clark & Elbing LLP; Susan M. Michaud

(57) ABSTRACT

The present invention provides compositions for use in recovering and/or ameliorating deterioration of physiological functions due to aging. Provided are: a cell overexpressing GDF6 protein or an miR-17 family member; a composition for use in treating a senescence-related condition, containing GDF6 protein; a composition for use in treating a senescence-related condition, containing a human expression vector for GDF6 protein or an miR-17 family member; and a composition for use in treating a senescence-related condition, containing a cell secreting GDF6 protein.

10 Claims, 10 Drawing Sheets

Specification includes a Sequence Listing.

(56) References Cited

OTHER PUBLICATIONS

Liao, et al. (2008) "Null mutations in human and mouse orthologs frequently result in different phenotypes", Proceedings of the National Academy of Science, USA, 105(19): 6987-92. (Year: 2008).*

Acosta et al., "A complex secretory program orchestrated by the inflammasome controls paracrine senescence," Nat Cell Biol. 15(8):978-90 (2013) (25 pages).

Acosta et al., "Chemokine signaling via the CXCR2 receptor reinforces senescence," Cell. 133(6):1006-18 (2008).

Asai-Coakwell et al., "GDF6, a novel locus for a spectrum of ocular developmental anomalies," Am J Hum Genet. 80(2):306-15 (2007).

Clendenning et al., "The BMP ligand Gdf6 prevents differentiation of coronal suture mesenchyme in early cranial development," PLoS One. 7(5):e36789 (2012) (9 pages).

Coppé et al., "Senescence-associated secretory phenotypes reveal cell-nonautonomous functions of oncogenic RAS and the p53 tumor suppressor," PLoS Biol. 6(12):2853-68 (2008).

Egerman et al., "GDF11 increases with age and inhibits skeletal muscle regeneration," Cell Metab. 22(1):164-74 (2015) (12 pages).

Hackl et al., "miR-17, miR-19b, miR-20a, and miR-106a are down-regulated in human aging," Aging Cell. 9(2):291-6 (2010).

Hisamatsu et al., "Growth differentiation factor 6 derived from mesenchymal stem/stromal cells reduces age-related functional deterioration in multiple tissues," Aging. 8(6):1259-69 (2016).

International Search Report for International Application No. PCT/JP2016/088865, dated Mar. 28, 2017, Kaneda, "Compositons for Recovering or Ameliorating Deterioration of Physiological Functions due to Aging," filed Dec. 27, 2016 (7 pages).

Kuilman et al., "Oncogene-induced senescence relayed by an interleukin-dependent inflammatory network," Cell. 133(6):1019-31 (2008).

Loffredo et al., "Growth differentiation factor 11 is a circulating factor that reverses age-related cardiac hypertrophy," Cell. 153(4):828-39 (2013).

Settle et al., "Multiple joint and skeletal patterning defects caused by single and double mutations in the mouse Gdf6 and Gdf5 genes," Dev Biol. 254(1):116-30 (2003).

Takahashi et al., "DNA damage signaling triggers degradation of histone methyltransferases through APC/C(Cdh1) in senescent cells," Mol Cell. 45(1):123-31 (2012).

Velarde et al., "Senescent cells and their secretory phenotype as targets for cancer therapy," Interdiscip Top Gerontol. 38:17-27 (2013).

Wang et al., "Differential expression of oncogenic miRNAs in proliferating and senescent human fibroblasts," Mol Cell Biochem. 352(1-2):271-9 (2011).

Wolfman et al., "Ectopic induction of tendon and ligament in rats by growth and differentiation factors 5, 6, and 7, members of the TGF-beta gene family," J Clin Invest. 100(2):321-30 (1997).

Yoshimoto et al., "Obesity-induced gut microbial metabolite promotes liver cancer through senescence secretome," Nature. 499(7546):97-101 (2013) (8 pages).

Jia et al., "MiR-17-5p modulates osteoblastic differentiation and cell proliferation by targeting SMAD7 in non-traumatic osteonecrosis," Exp. Mol. Med. 46(7):e107 (2014) (8 pages).

Li et al., "miR-17-5p and miR-106a are involved in the balance between osteogenic and adipogenic differentiation of adipose-derived mesenchymal stem cells," Stem Cell Res. 10(3):313-324 (2013).

Official Communication dated Oct. 6, 2020 for Japanese Patent Application No. 2017-559201, Kaneda et al., "A composition for restoring or improving deterioration of physiological functions due to aging," filed Dec. 27, 2016 (4 pages).

* cited by examiner

FIG. 2
a
| | Young | Old | Old/Young ratio |
|---|---|---|---|
| miR-17 | 1.06 | 0.42 | 0.40 |
| miR-18a | 6.89 | 2.53 | 0.37 |
| miR-19a | 0.73 | 0.39 | 0.54 |
| miR-19b | 1.49 | 0.60 | 0.41 |
| miR-20a | 0.82 | 0.31 | 0.38 |
| miR-20b | 1.78 | 0.66 | 0.37 |
| miR-106a | 1.21 | 0.58 | 0.48 |
| miR-106b | 0.90 | 0.40 | 0.44 |
| miR-25 | 0.76 | 0.44 | 0.58 |
| miR-92a | 0.60 | 0.21 | 0.34 |
| miR-93 | 0.89 | 0.36 | 0.40 |
| miR-363 | 0.73 | 0.27 | 0.37 |
b
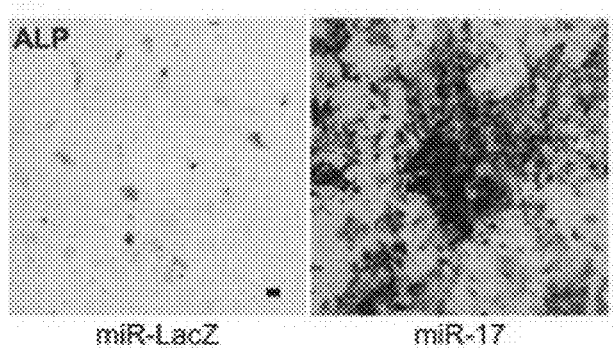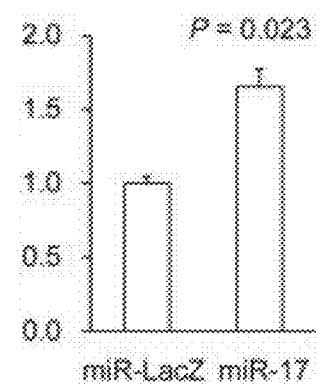
c
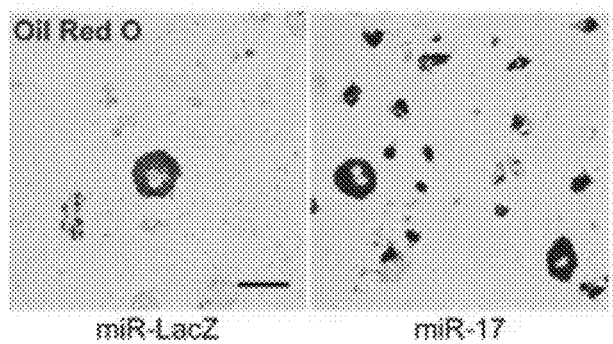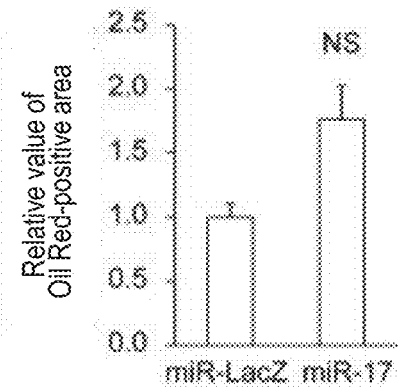

FIG. 5
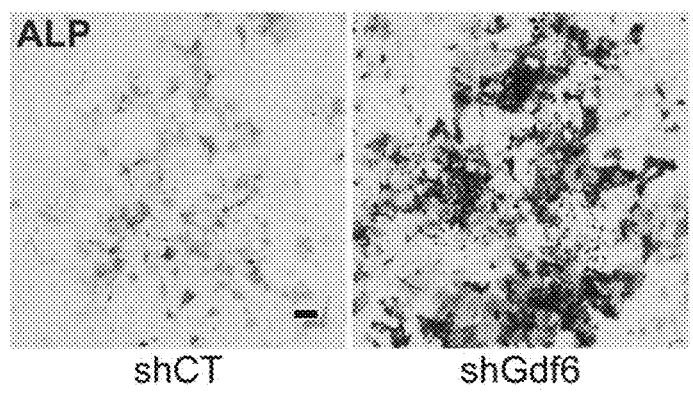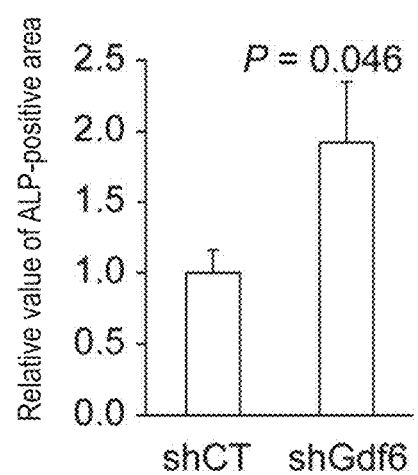
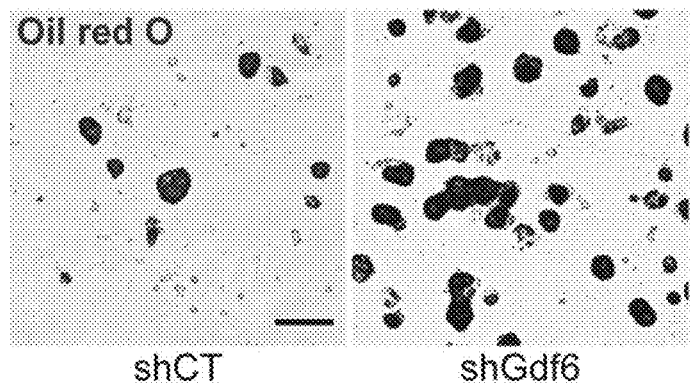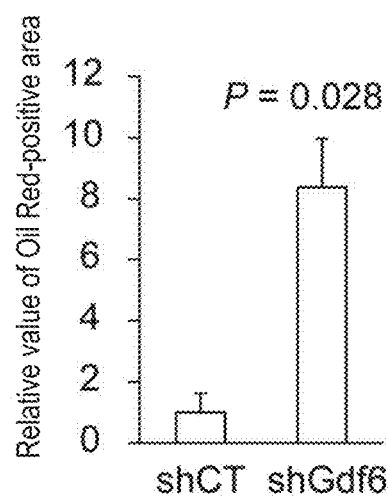

FIG. 7
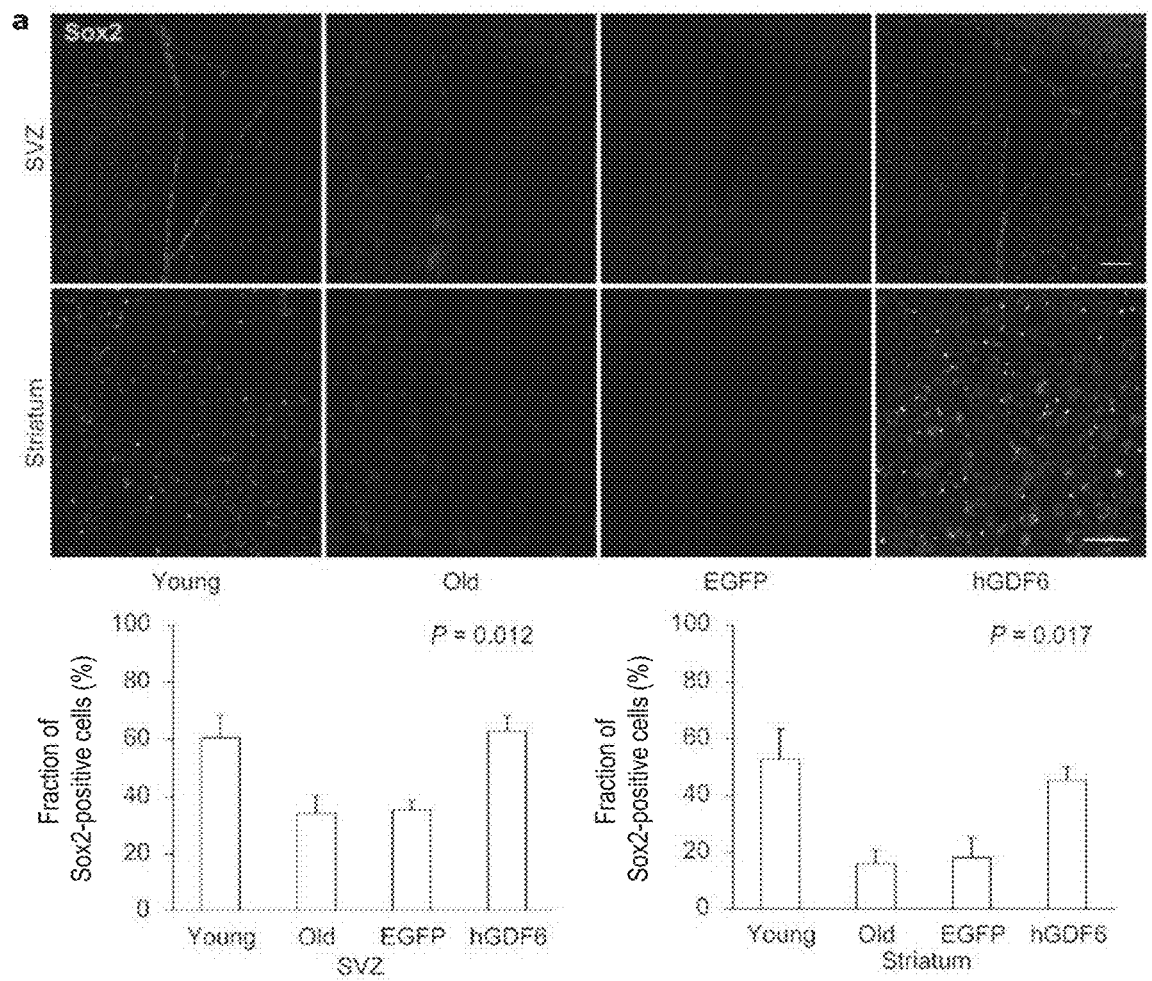
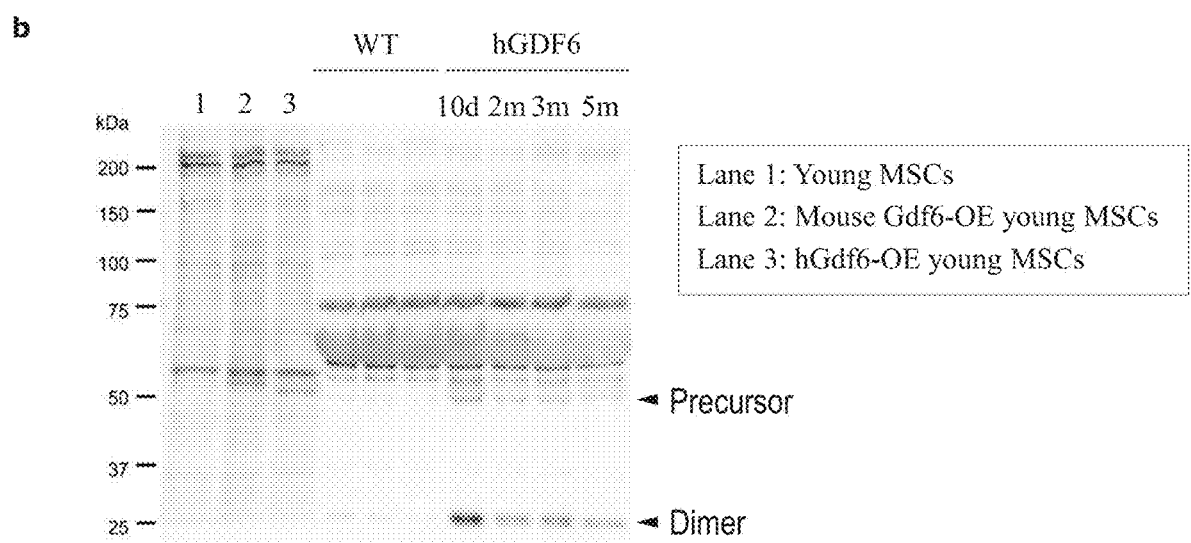

COMPOSITIONS FOR USE IN RECOVERING OR AMELIORATING DETERIORATION OF PHYSIOLOGICAL FUNCTIONS DUE TO AGING

TECHNICAL FIELD

The present invention relates to compositions for use in recovering or ameliorating deterioration of physiological functions due to aging.

BACKGROUND OF INVENTION

GDF6 is a member of the transforming growth factor β (TGF-β) family, and was cloned in Non Patent Literature 1 for the first time. GDF6 is also called BMP-13 or CDMP-2. Human GDF6 is a protein consisting of 455 amino acids (molecular weight: approximately 50 kDa), and is encoded by a nucleotide sequence as set forth in SEQ ID NO: 1, and has an amino acid sequence as set forth in SEQ ID NO: 2. Human GDF6 is subjected to cleavage during the maturing process and converted into a mature protein consisting of 120 amino acids as set forth in SEQ ID NO: 3. The mature protein forms a dimer (in particular, a homodimer) under physiological conditions, and expresses physiological function as GDF6. The function of GDF6 protein is believed to be involved in formation of the eyeballs, skull, bones of the feet, and joints (Non Patent Literatures 2 to 4).

GDF11, which is a member of the TGF-β family, has been reported to be expressed at a lower expression level in association with senescence, and to be applicable to treatment of senescence-related conditions (e.g., heart failure) (Patent Literature 1, Non Patent Literature 5). In contrast, GDF11 has been also reported to be expressed at a higher expression level in association with senescence to lower the regenerative ability for muscles (Non Patent Literature 6).

Senescence is well known to cause change in condition such as muscle reduction, thinning of skin tissue, reduction of the vascular network, reduction of lymphocytes, reduction of nerve cells, loss of hair, and gray hair, and in addition result in condition of an age-related disease such as cancer, Alzheimer's disease, arteriosclerosis, osteoporosis, and pulmonary fibrosis, or condition with a high possibility thereof. Moreover, senescence leads to presentation of the symptoms of geriatric syndrome such as neurocognitive disorder, delirium, senile depression, motor deficits, chronic dizziness, anorexia, and deterioration of wound-healing ability, although each of these conditions is not clear pathological condition like age-related diseases. Each of these conditions is individual senescence, which is found for living tissue or an individual organism. In terms of microscopic change in condition, cellular senescence is also included in senescence-related conditions.

It has been reported that cells affected by cellular senescence (senescent cells) are highly expressing various secretion factors including inflammatory cytokines, chemokines, MMPs (matrix metalloproteases), and growth factors. Such a phenomenon that inflammatory cytokines and the like are secreted in association with cellular senescence is called SASP (Senescence-Associated Secretory Phenotype), and proteins secreted are collectively referred to as SASP factors (Non Patent Literatures 7 to 9). In addition, the SASP factors are reported to exert paracrine effect on cells therearound to induce cellular senescence (Non Patent Literature 10), and thus are factors to accelerate not only phenomena caused by cellular senescence but also senescence in various sites in the body. Moreover, the SASP factors are noted to cause chronic inflammation, worsen various conditions, and lead to generation of cancer, and the relation with individual senescence is suggested (Non Patent Literatures 11 to 13).

CITATION LIST

Patent Literature

Patent Literature 1: International Publication No. WO 2013/142,114

Non Patent Literature

Non Patent Literature 1: Wolfman et al., J. Clin. Invest., 100 (2): 321-330, 1997
Non Patent Literature 2: Asai-Coakwell M. et al., Am. J. Hum. Genet., 80, 306-315, 2007
Non Patent Literature 3: Clendenning D E and Mortlock D P, PLoS One, 7, e36789, 2012
Non Patent Literature 4: Settle S H Jr. et al., Dev. Biol., 254, 116-130, 2003
Non Patent Literature 5: Loffredo et al., Cell, 153, 828-839, 2013
Non Patent Literature 6: Egerman M A et al., Cell Metab, 22, 164-174, 2015
Non Patent Literature 7: Acosta et al., Cell, 133, 1006-18, 2008
Non Patent Literature 8: Kuilman et al., Cell, 133, 1019-31, 2008
Non Patent Literature 9: Coppe et al., PLoS Biol., 6, 2853-68, 2008
Non Patent Literature 10: Acosta et al., Nat Cell Biol., 8, 978-90, 2013
Non Patent Literature 11: Takahashi et al., Mol Cell., 45, 123-31, 2012
Non Patent Literature 12: Velarde M C et al., Interdiscip Top Gerontol., 38, 17-27, 2013
Non Patent Literature 13: Yoshimoto et al., Nature, 499, 97-101, 2013

SUMMARY OF INVENTION

The present invention provides compositions for recovering or ameliorating deterioration of physiological functions due to aging.

The present inventors found that a mesenchymal stem/stromal cell (hereinafter, also referred to as MSC) in the young age secretes GDF6 protein as a humoral factor, that expression of Gdf6 is lowered through aging, that expression of miR-17 family members is lowered through aging, and that suppression of expression of the miR-17 family leads to lowering of expression of Gdf6 even in the young age. At the same time, the present inventors found that Gdf6 protein functions as a potential regeneration factor for tissue stem cells, that Gdf6 protein lowers the blood level of SASP factors, and that recovery or amelioration of deterioration of physiological functions due to aging is induced via Gdf6 protein. The present invention was made on the basis of these findings.

Specifically, the present invention provides the followings.
(1) A composition for use in treating a senescence-related condition, containing GDF6 protein or an miR-17 family member.
(2) A composition for use in treating a senescence-related condition, containing a human expression vector for GDF6 protein or an miR-17 family member.

(3) A composition for use in treating a senescence-related condition, containing a cell secreting GDF6 protein.
(4) A cell overexpressing GDF6 protein or an miR-17 family member.
(5) The cell according to (4) obtained by allowing a mesenchymal stem/stromal cell or blood cell to overexpress GDF6 protein or an miR-17 family member.
(6) The cell according to (5), wherein the mesenchymal stem/stromal cell or blood cell is a senescent cell.
(7) The cell according to any one of (4) to (6), wherein the cell is a human cell.
(8) The composition according to (3), wherein the cell is the cell according to any one of (4) to (7).
(9) The composition according to any one of (1) to (3) and (8), wherein the GDF6 protein has:
  (i) an amino acid sequence as set forth in SEQ ID NO: 2 or 3;
  (ii) a sequence having 90% or higher homology with an amino acid sequence as set forth in SEQ ID NO: 2 or 3;
  (iii) an amino acid sequence obtained by providing an amino acid sequence as set forth in SEQ ID NO: 2 or 3 with deletion, insertion, and/or substitution of 1 to 10 amino acids; or
  (iv) an amino acid sequence encoded by a sequence hybridizable with a nucleic acid having a sequence complementary to a DNA sequence encoding an amino acid sequence as set forth in SEQ ID NO: 2 or 3 under stringent conditions.
(10) The composition according to (1), (2), or (8), wherein the miR-17 family member has:
  (i) a nucleic acid sequence as set forth in SEQ ID NO: 4;
  (ii) 90% or higher identity with a nucleic acid sequence as set forth in SEQ ID NO: 4; or
  (iii) a nucleic acid sequence obtained by providing a nucleic acid sequence as set forth in SEQ ID NO: 4 with deletion, insertion, and/or substitution of 1 to 10 nucleotides.
(11) The composition according to any one of (1) to (3) and (8) to (10), wherein the senescence-related condition is muscle senescence, senescence of the hematopoietic system, senescence of the nervous system, senescence of the vascular system, senescence of skin tissue, senescence of hair, or cellular senescence.
(12) The composition according to any one of (1) to (3) and (8) to (10), wherein the senescence-related condition is at least one of the following conditions associated with senescence: lowering of resilience to muscle injury, reduction of lymphocytes, reduction of neural stem/precursor cells, hardening of blood vessel walls, narrowing of the vascular lumen, reduction of the vascular network, lowering of the elasticity of skin tissue, thinning of skin tissue, deterioration of hair glossiness, reduction of undifferentiated cells, and increase in secretion of SASP factors.
(13) The cell according to any one of (4) to (7), wherein the GDF6 protein has:
  (i) an amino acid sequence as set forth in SEQ ID NO: 2 or 3;
  (ii) a sequence having 90% or higher homology with an amino acid sequence as set forth in SEQ ID NO: 2 or 3;
  (iii) an amino acid sequence obtained by providing an amino acid sequence as set forth in SEQ ID NO: 2 or 3 with deletion, insertion, and/or substitution of 1 to 10 amino acids; or
  (iv) an amino acid sequence encoded by a sequence hybridizable with a nucleic acid having a sequence complementary to a DNA sequence encoding an amino acid sequence as set forth in SEQ ID NO: 2 or 3 under stringent conditions.
(14) The cell according to any one of (4) to (7), wherein the miR-17 family member has:
  (i) a nucleic acid sequence as set forth in SEQ ID NO: 4;
  (ii) 90% or higher identity with a nucleic acid sequence as set forth in SEQ ID NO: 4; or
  (iii) a nucleic acid sequence obtained by providing a nucleic acid sequence as set forth in SEQ ID NO: 4 with deletion, insertion, and/or substitution of 1 to 10 nucleotides.

The present invention enables recovery or amelioration of deterioration of physiological functions due to aging. In particular, the finding that GDF6 lowered the plasma protein concentration for various SASP factors (inflammatory cytokines and/or chemokines), which had been reported to have senescence-accelerating effect, secreted by senescent cells suggests not only that GDF6 ameliorates deterioration of cell functions but also that GDF6 ameliorates systemic deterioration of physiological functions due to aging. The present invention is also useful for amelioration of condition of an age-related disease such as cancer, Alzheimer's disease, arteriosclerosis, osteoporosis, and pulmonary fibrosis, or condition with the possibility thereof.

BRIEF DESCRIPTION OF DRAWINGS

FIG. 2 shows change in the amount of expression of miR-17 family members between young MSCs and old MSCs (FIG. 2a) and impact on the potency of differentiation into an osteocyte and the potency of differentiation into an adipocyte in cells with overexpression of miR-17 (FIGS. 2b and 2c).

FIGS. 4c and 4d show that Gdf6 particularly has strong action to recover and/or ameliorate deterioration of physiological functions due to aging among 13 candidate genes identified; FIG. 4e shows expression of Bmp2/4; and FIG. 4f shows change in potency of differentiation of an MSC into an osteocyte by BMP2.

FIG. 5 shows impact of Gdf6 knock-down on the potency of differentiation of cells.

FIG. 6a illustrates a scheme of the intraperitoneal administration of viruses for overexpression of GDF6 to an old mouse; FIG. 6b shows recovery effect of GDF6 overexpression on decrease in the number of lymphocytes in an old mouse; and FIG. 6c shows recovery effect of GDF6 overexpression on regenerative ability for muscles in an old mouse.

FIG. 7a shows effect to increase the number of neural precursor cells in the brain of an old mouse with overexpression of GDF6; and FIG. 7b shows results of Western blotting to confirm expression of GDF6 protein in the plasma.

FIG. 10 also shows the increase in the amount of blood vessels in a brain tissue section from an old mouse with overexpression of GDF6 (right).

FIG. 11 also shows the increase in the number of neuroblasts in a brain tissue section from an old mouse with overexpression of GDF6 (right).

DETAILED DESCRIPTION OF THE INVENTIONS

Figure 1:
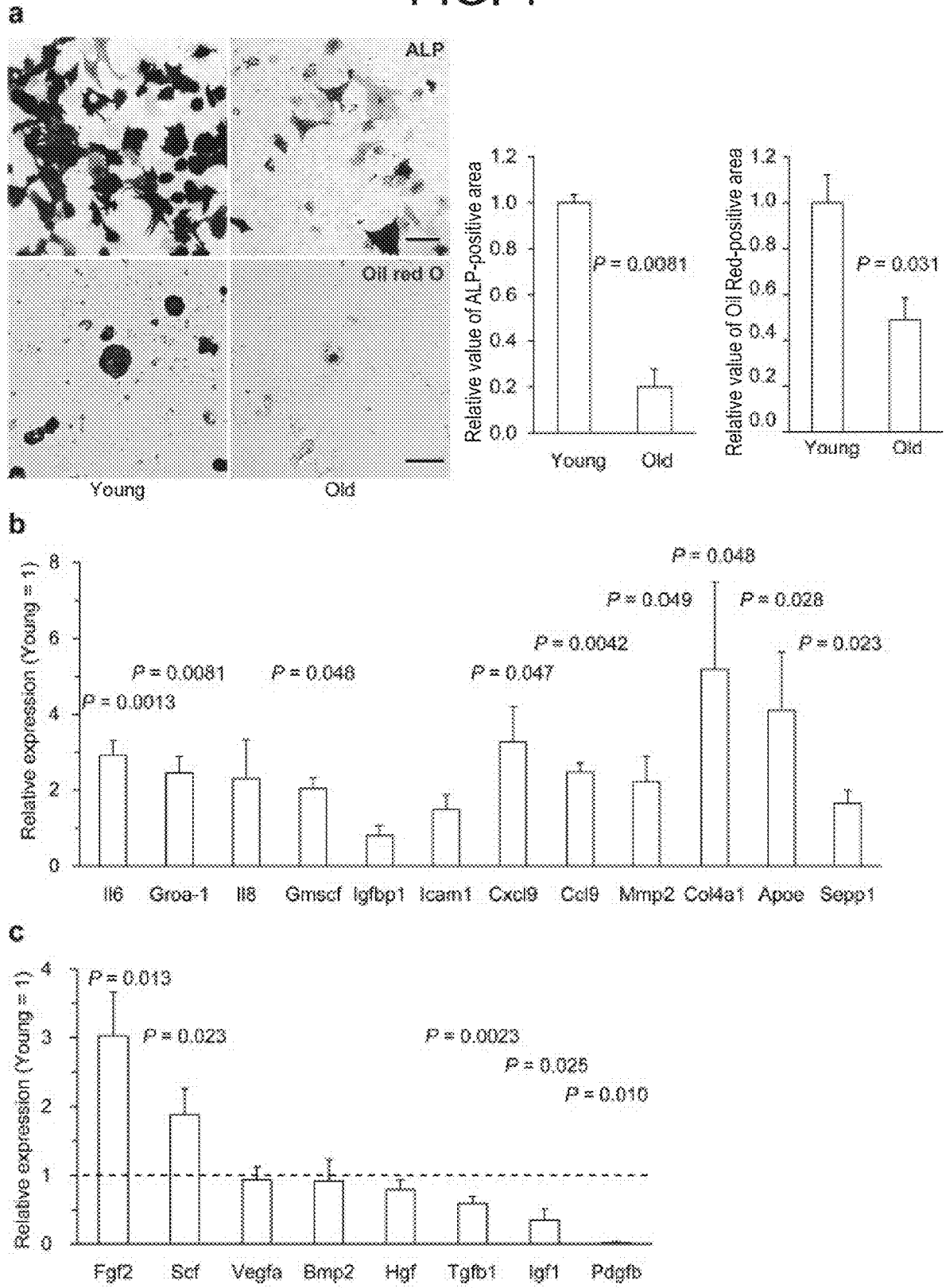
FIG. 1 shows difference in the potency of differentiation into an osteoblast and the potency of differentiation into an adipocyte (FIG. 1a), difference in expression of Senescence-Associated Secretory Phenotype (SASP)-like inflammatory factors (FIG. 1b), and difference in expression of growth factors (FIG. 1c) between young mesenchymal stem/stromal cells (MSCs) and old MSCs.

The term "cell preparation" as used herein refers to a composition which is to be administered to a subject for treatment of condition of deteriorated physiological functions and contains cells as an active ingredient. The term "protein preparation" as used herein refers to a composition containing protein as an active ingredient.

The term "senescence-related condition" or an expression similar thereto as used herein refers to condition resulting from deterioration of physiological functions of cells and/or tissue due to aging. Examples of the senescence-related condition include, but are not limited to, reduction of lymphocytes (or deterioration of the capability to produce lymphocytes), reduction of nerve cells, muscle reduction, thinning of skin tissue, reduction of the vascular network, and increase in cells with cellular senescence (senescent cells). Other examples of the senescence-related condition include deterioration of the brain function; deterioration of physiological functions such as increase in the incidence rate of infections, increase in the incidence rate of cancers, lowering of resilience to muscle injury, deterioration of wound-healing ability, hardening of blood vessel walls, narrowing of the vascular lumen, lowering of the elasticity of skin tissue, and deterioration of hair glossiness; and age-related diseases and geriatric syndrome caused by such conditions. Examples of condition of cellular senescence include accumulation of DNA damage in cells, reduction or loss of Sox2-positive neural precursor cells, deterioration of the regenerative ability of tissue stem cells, and increase in secretion of senescence-associated secretory phenotype (SASP) factors in association with cellular senescence. Examples of SASP factors, secretion of which increases in association with cellular senescence, include inflammatory cytokines, chemokines, MMPs (matrix metalloproteases), and growth factors. More specifically, the inflammatory cytokine is, for example, IL-1a, IL-1b, IL-6, IL-17, interferon β, and/or G-SCF, and the chemokine is, for example, CCL3, CCL4, CCL11, and/or MCP-1. Increase in secretion of SASP factors can be confirmed as increase in the blood concentration.

The term "treatment" as used herein refers to "therapy" and/or "prophylaxis". The term "therapy" as used herein refers to delaying deterioration of condition, preventing deterioration of condition, or ameliorating condition. The term "prophylaxis" as used herein refers to suppressing the onset of condition.

With respect to the term "stringent conditions" as used herein, conditions such that washing is performed, for example, with 0.1×SSC and 0.1% SDS at 65° C. after hybridization can be employed.

The term "overexpression" as used herein refers to a state in which a larger amount of intended protein is expressed in a targeted cell through introduction of an exogenous nucleic acid (including DNA, RNA, artificial nucleotide, and combination thereof) encoding the intended protein into the targeted cell than in the case of a cell without such introduction, or a state in which intended protein which is not expressed in a cell without such introduction has become expressed. Methods for allowing a cell to overexpress protein or nucleic acid are well known to those skilled in the art, and examples of the method include, but are not limited to, introduction with viruses such as lentiviruses, adenoviruses, and Sendai viruses.

According to the present invention, GDF6 protein functions as a humoral factor, and flows through the blood of a senescent subject to spread over the whole body, and exerts the action to recover and/or ameliorate deterioration of physiological functions due to aging in the senescent subject. Specifically, conditions associated with senescence including reduction of lymphocytes (e.g., reduction of B-cells and/or T-cells), muscle reduction, nerve reduction, reduction of the vascular network, deterioration of hair glossiness, reduction of undifferentiated cells such as Sox2-expressing cells, and the blood concentration of SASP factors in an old mouse were ameliorated through overexpression of GDF6 protein. In other words, GDF6 protein was found to have effect to ameliorate condition associated with senescence, the effect including increase in lymphocytes (e.g., increase in B-cells and/or T-cells), increase in muscle regeneration, increase in neurogenesis, increase in blood vessels or the vascular network, amelioration of hair glossiness (enhanced glossiness), increase in undifferentiated cells such as Sox2-expressing cells, and lowering of the blood concentration of SASP factors. Thus, the present inventors revealed that GDF6 protein recovers and/or ameliorates deterioration of physiological functions due to aging in an old mouse.

Accordingly, the present invention provides a vector for allowing cells to express GDF6, and a composition containing the vector for use in recovering and/or ameliorating deterioration of physiological functions due to aging. In addition, the present invention provides a cell (e.g., a blood cell or MSC) secreting GDF6 protein, and a composition containing the cell for use in recovering and/or ameliorating deterioration of physiological functions due to aging. Further, the present invention provides a composition containing GDF6 protein, such as a protein preparation, for use in recovering and/or ameliorating deterioration of physiological functions due to aging. Furthermore, the present invention provides a composition containing a cell secreting GDF6 protein, such as a cell preparation, for use in recovering and/or ameliorating deterioration of physiological functions due to aging.

These compositions can be used for use in ameliorating condition accompanied by senescence, for example, recovering and/or ameliorating deterioration of physiological functions due to aging in a senescent subject. In a certain embodiment, the composition according to the present invention is a composition for use in ameliorating reduction of lymphocytes in association with senescence and/or the function of lymphocytes in a senescent subject. In a certain embodiment, the composition according to the present invention can be a composition for use in ameliorating reduction of myocytes in association with senescence and/or the function of myocytes in a senescent subject. In a certain embodiment, the composition according to the present invention can be a composition for use in ameliorating reduction of neural precursor cells in association with senescence and/or the function of neural precursor cells in a senescent subject. The composition according to the present invention can be a composition for use in ameliorating reduction of the vascular network in association with senescence in a senescent subject. In a certain embodiment, the composition according to the present invention can be a composition for use in ameliorating deterioration of wound-healing ability in association with senescence in a senescent subject. In a certain embodiment, the composition according to the present invention can be a composition for use in ameliorating deterioration of wound-healing ability for muscles in association with senescence in a senescent subject. In a certain embodiment, the composition according to the present invention can be a composition for use in recovering reduction of undifferentiated cells (e.g., reduction of Sox2-expressing cells) in association with senescence in a senescent subject. In a certain embodiment, the composition according to the present invention can be a composition for use in lowering the blood level of SASP factors (e.g., IL-1b, IL-6, IL-17, G-SCF, CCL11, MCP-1, CCL3, and/or CCL4) in a senescent subject. In addition, these compositions can be a composition for use in ameliorating condition associated with senescence, including increase in lymphocytes (e.g., increase in B-cells and/or T-cells), increase in muscle regeneration, increase in neurogenesis, increase in blood vessels or the vascular network, amelioration of hair glossiness (enhanced glossiness), increase in undifferentiated cells such as Sox2-expressing cells, and lowering of the blood concentration of SASP factors.

The subject in the present invention is a mammal (e.g., a human) being senescent or suspected to be senescent. The human who is senescent or suspected to be senescent is, for example, a human aged 20 years or older, preferably a human aged 40 years or older, a human aged 45 years or older, a human aged 50 years or older, a human aged 55 years or older, a human aged 60 years or older, a human aged 65 years or older, a human aged 70 years or older, a human aged 75 years or older, or a human aged 80 years or older, although the age differs among individuals. The presence or absence of senescence can be easily determined by a physician or the like on the basis of the presence or absence of deterioration of defense against infection, deterioration of memory ability, and other condition associated with senescence.

GDF6 protein to be used in the present invention is inferred to exert the activity as mature protein (activated form) consisting of 120 amino acids derived from intramolecular cleavage of GDF6 protein through protein processing. Accordingly, GDF6 protein to be used in the present invention in a preferred embodiment of the present invention may be an activated form of GDF6 protein, for example, a protein having:

(i) an amino acid sequence as set forth in SEQ ID NO: 3.

Alternatively, GDF6 protein to be used in the present invention in another preferred embodiment can be a protein having:

(ii) a sequence having 90% or higher homology (or identity), preferably having 95% or higher homology (or identity), more preferably having 98% or higher homology (or identity), even more preferably 99% or higher homology (or identity), with an amino acid sequence as set forth in SEQ ID NO: 3; or (iii) an amino acid sequence obtained by providing an amino acid sequence as set forth in SEQ ID NO: 3 with deletion, insertion, and/or substitution of 1 to 10 amino acids, preferably of one to five amino acids, more preferably of one to three amino acids, even more preferably of one amino acid. In the present invention, the activated form of GDF6 protein can form a homodimer.

Proteins belonging to the TGFβ family are each known to form a precursor which is then decomposed by protease outside of cells. GDF6 is believed to be decomposed by protease outside of cells, similarly after the formation of the precursor. Accordingly, GDF6 protein to be used in the present invention in another preferred embodiment of the present invention can be a precursor form, for example, a protein having:

(i) an amino acid sequence as set forth in SEQ ID NO: 2.

Alternatively, GDF6 protein to be used in the present invention in another preferred embodiment can be a protein having:

(ii) a sequence having 90% or higher homology (or identity), preferably having 95% or higher homology (or identity), more preferably having 98% or higher homology (or identity), even more preferably 99% or higher homology (or identity), with an amino acid sequence as set forth in SEQ ID NO: 2; or (iii) an amino acid sequence obtained by providing an amino acid sequence as set forth in SEQ ID NO: 2 with deletion, insertion, and/or substitution of 1 to 10 amino acids, preferably of one to five amino acids, more preferably of one to three amino acids, even more preferably of one amino acid. In the present invention, the precursor form of GDF6 protein can form a homodimer. In order for the precursor form to be converted into the activated form, it is preferred that the amino acid sequence corresponding to positions 331 to 335 of the amino acid sequence as set forth in SEQ ID NO: 2 be retained. Thus, in the case that GDF6 protein to be used in the present invention is provided as the precursor form, it is preferred to use GDF protein in which the amino acid sequence corresponding to positions 331 to 335 of the amino acid sequence as set forth in SEQ ID NO: 2 is retained, or an RXXR motif (where X represents any amino acid) is retained.

"Homology" herein can be determined by using a BLAST program provided by the National Center for Biotechnology Information (NCBI) with default parameters (initial setting) (see http://blast.ncbi.nlm.nih.gov/Blast.cgi). "Identity" is determined from the number of accurately matched sequences between two aligned sequences. Alignment can be performed by using ClustalW Ver. 2 with default parameters.

Figure 4:
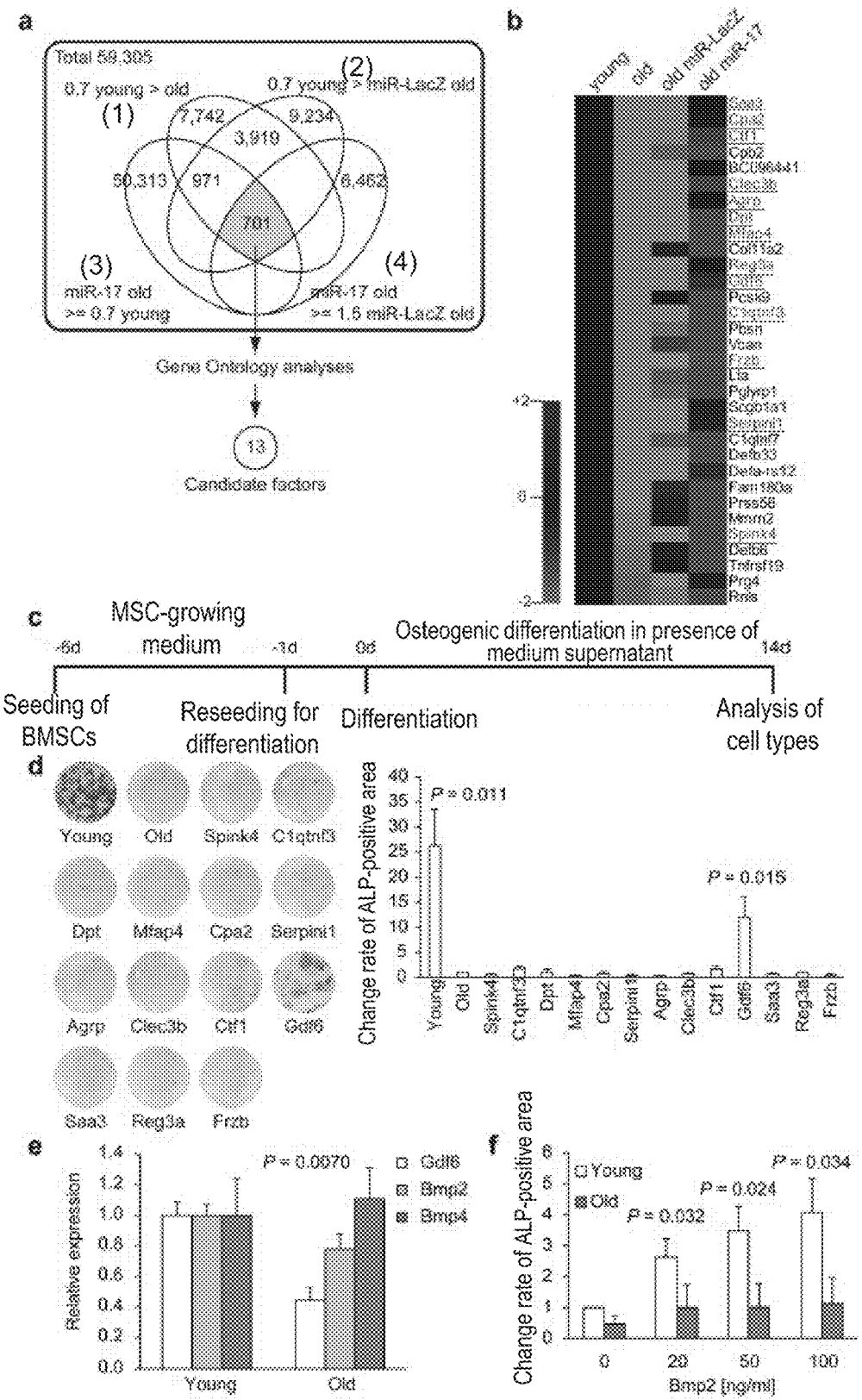
FIG. 4 shows results of screening for secretion factors whose amount of expression decreases in association with senescence and recovers through overexpression of miR-17 in MSCs overexpressing miR-17 (FIGS. 4a and 4b)

GDF6 is a growth factor belonging to the TGFβ family, and the effect to recover and/or ameliorate deterioration of physiological functions due to aging in a senescent subject is inferred to be due to the activity as a growth factor. For example, even BMP2/4, which share TGFβ receptors (specifically, ALK3/6) and Smad1/5/8, exhibit the function in a partial manner, although the function is weaker (FIG. 4f). Accordingly, the effect of GDF6 to recover and/or ameliorate deterioration of physiological functions due to aging is expected to be partially due to activation of ALK3/6. Thus, GDF6 protein to be used in the present invention in a preferred embodiment of the present invention may have ALK3/6 activation potential. In other words, GDF6 protein to be used in the present invention in a preferred embodiment of the present invention, specifically, the protein having (ii) a sequence having 90% or higher homology, preferably having 95% or higher homology, more preferably having 98% or higher homology, even more preferably 99% or higher homology, with a protein having an amino acid sequence as set forth in SEQ ID NO: 3 may have ALK3/6 activation capability, and the protein having (iii) an amino acid sequence obtained by providing an amino acid sequence as set forth in SEQ ID NO: 3 with deletion, insertion, and/or substitution of 1 to 10 amino acids, preferably of one to five amino acids, more preferably of one to three amino acids, even more preferably of one amino acid may have ALK3/6 activation capability.

The present invention provides an intracellular expression vector including a nucleic acid sequence in which a nucleic acid sequence encoding GDF6 protein to be used in the present invention is operably linked to a promoter. A nucleic acid having a sequence hybridizable with a complementary sequence to a nucleic acid sequence encoding GDF6 protein to be used in the present invention under stringent conditions may be used for the expression vector according to the present invention. The intracellular expression vector according to the present invention can be used as an expression vector for human. The vector according to the present invention may have an origin of replication which enables replication in microorganisms such as yeasts and *Escherichia coli*. The vector according to the present invention may have an origin of replication which enables replication in the human body, or may be a vector which does not allow replication in the human body in consideration of safety. Virus vectors well known to those skilled in the art such as adenoviruses, lentiviruses, and retroviruses can be used for the vector. In consideration of further safety, an mRNA itself encoding GDF6 protein may be administered to a subject in the case that temporary expression is intended. GDF6 protein can be obtained from a cell expressing GDF6 by using a method well known to those skilled in the art. Known are, for example, a method in which GDF6 protein is expressed as a tag-fused protein and purified by using the tag, a method utilizing the principle of immunoprecipitation with an anti-GDF6 antibody, a method of expressing GDF6 protein by using a cell-free extract system, and a method of producing GDF6 protein by using chromatography.

In the case that a part of the amino acids of GDF6 protein is substituted, conservative substitution is applicable in a certain embodiment. The term "conservative substitution" refers to substitution of an amino acid with another amino acid having similar characteristics. Non-limiting examples of conservative substitution are substitutions among members belonging to any one group of the following groups: a group consisting of acidic amino acids including glutamic acid and aspartic acid; a group consisting of basic amino acids including lysine and arginine; a group consisting of hydrophobic amino acids including leucine, alanine, glycine, and isoleucine; a group consisting of polar amino acids including glutamine, histidine, methionine, and asparagine; a group consisting of aromatic amino acids including tryptophan, tyrosine, and phenylalanine; a group consisting of low-molecular-weight amino acids including glycine, alanine, serine, and threonine; and a group consisting of sulfur-containing amino acids including cysteine and methionine.

The present invention provides a composition, such as a cell preparation, for use in treating a senescence-related condition, containing a cell secreting GDF6 protein. GDF6 protein can be secreted as a precursor. The cell secreting GDF6 protein can be obtained, for example, through allowing a cell to overexpress GDF6 protein. Examples of cells applicable as the cell secreting GDF6 protein include, but are not limited to, cells obtained through allowing blood cells or MSCs to overexpress GDF6 protein. The blood cells may be consisting of one type of cells or a cell group as a mixture of multiple types of cells, and, for example, peripheral blood collected from a subject may be used. In a certain embodiment, erythrocytes or leukocytes can be used as the blood cells. Neutrophils, eosinophils, basophils, lymphocytes, or monocytes can be used as the leukocytes. Memory B-cells, memory T-cells, or the like, as long-life cells, may be used as the lymphocytes. Methods for allowing these cells to express GDF6 protein are well known to those skilled in the art. In a certain embodiment of the present invention, the cell secreting GDF6 protein may be a GDF6 protein-secreting cell isolated from a mammal, preferably, isolated from a human.

In a certain embodiment of the present invention, the cell secreting GDF6 protein may be obtained through allowing senescent cells derived from a senescent subject to overexpress GDF6 protein.

According to the present invention, GDF6 protein can be secreted through allowing cells to overexpress an miR-17 family member. Accordingly, the cell overexpressing GDF6 protein in the present invention may be obtained as a cell with overexpression of an miR-17 family member. According to the present invention, overexpression of GDF6 protein was achieved through allowing cells to overexpress an miR-17 family member, even in the case that the cells were senescent cells. Accordingly, the cell overexpressing GDF6 protein can obtained even through allowing senescent cells to overexpress an miR-17 family member in a certain embodiment of the present invention. In a certain embodiment of the present invention, the senescent cells can be MSCs or blood cells derived from a subject being senescent or suspected to be senescent. Methods for allowing these cells to express an miR-17 family member are well known to those skilled in the art.

The term "miR-17 family member" refers to one or more microRNAs selected from a group consisting of miR-17, miR-106a, miR-106b, miR-20a, miR-20b, and miR-93, and the miR-17 family member is preferably miR-17. The term "miR-17" encompasses both the precursor and mature form of the microRNA. The miR-17 precursor has, for example, a nucleotide sequence as set forth in SEQ ID NO: 4. Examples of the mature miR-17 include SEQ ID NO: 5 (miR-17-5p) and SEQ ID NO: 6 (miR-17-3p). The miR-20a precursor has, for example, a nucleotide sequence as set forth in SEQ ID NO: 7, and examples of the mature miR-20a include SEQ ID NO: 8 (miR-20a-5p) and SEQ ID NO: 9 (miR-20a-3p). The miR-106b precursor has, for example, SEQ ID NO: 10, and examples of the mature miR-106b include SEQ ID NO: 11 (miR-106b-5p) and SEQ ID NO: 12 (miR-106b-3p). The miR-93 precursor has, for example, SEQ ID NO: 13, and examples of the mature miR-93 include SEQ ID NO: 14 (miR-93-5p) and SEQ ID NO: 15 (miR-93-3p). The miR-106a precursor has, for example, SEQ ID NO: 16, and examples of the mature miR-106a include SEQ ID NO: 17 (miR-106a-5p) and SEQ ID NO: 18 (miR-106a-3p). The miR-20b precursor has, for example, a nucleotide sequence as set forth in SEQ ID NO: 19, and examples of the mature miR-20b include SEQ ID NO: 20 (miR-20b-5p) and SEQ ID NO: 21 (miR-20b-3p). The miR-17 family member may have any sequence which can introduce expression of GDF6 protein. For example, an RNA having:
  (i) any one of nucleic acid sequences as set forth in SEQ ID NOs: 4 to 21;
  (ii) 90% or higher identity with any one of nucleic acid sequences as set forth in SEQ ID NOs: 4 to 21; or
  (iii) a nucleic acid sequence obtained by providing any one of nucleic acid sequences as set forth in SEQ ID NOs: 4 to 21 with deletion, insertion, and/or substitution of 1 to 10 nucleotides, preferably of one to five nucleotides, more preferably of one to three nucleotides, even more preferably of one or two nucleotides, furthermore preferably of one nucleotide, can be used as the miR-17 family member. For example, an RNA having:
  (i) a nucleic acid sequence as set forth in SEQ ID NO: 4;
  (ii) 90% or higher identity with a nucleic acid sequence as set forth in SEQ ID NO: 4; or
  (iii) a nucleic acid sequence obtained by providing a nucleic acid sequence as set forth in SEQ ID NO: 4 with deletion, insertion, and/or substitution of 1 to 10 nucleotides, preferably of one to five nucleotides, more preferably of one to three nucleotides, even more preferably of one or two nucleotides, furthermore preferably of one nucleotide,
can be used as the miR-17 family member. Whether the miR-17 family member induces expression of GDF6 protein can be evaluated, for example, through analysis by using Western blotting for a cell overexpressing the miR-17 family member or culture supernatant therefor.

The present invention provides a composition, such as a cell preparation, for use in treating a senescence-related condition, containing the miR-17 family member.

The present invention provides an intracellular expression vector including a nucleic acid sequence in which a DNA encoding the miR-17 family member is operably linked to a promoter. The intracellular expression vector according to the present invention can be an expression vector for human. The vector according to the present invention may have an origin of replication which enables replication in microorganisms such as yeasts and *Escherichia coli*. The vector according to the present invention may have an origin of replication which enables replication in the human body, or may be a vector which does not allow replication in the human body in consideration of safety. Virus vectors well known to those skilled in the art such as adenoviruses, lentiviruses, and retroviruses can be used for the vector. In consideration of further safety, the miRNA itself may be administered to a subject in the case that temporary expression is intended. The vector for expression of the miR-17 family member can be produced by using a method well known to those skilled in the art. The microRNA can be prepared by using a method well known to those skilled in the art. For example, a method of purifying a microRNA from a cell extract by using an anti-Ago2 antibody is known.

The cell preparation according to the present invention may contain a pharmaceutically acceptable diluent, carrier, or vehicle in addition to a cell. The cell preparation according to the present invention can be parenterally administered, for example, through intravenous administration, intracavitary administration, intracerebroventricular administration, intracardioventricular administration, intraperitoneal administration, subcutaneous administration, or intramuscular administration, but the route of administration is not limited thereto. The cell preparation according to the present invention may be used as a pharmaceutical composition.

The protein preparation according to the present invention may contain a pharmaceutically acceptable diluent, carrier, or vehicle in addition to GDF6 protein. The protein preparation according to the present invention can be parenterally administered, for example, through intravenous administration, intracavitary administration, intracardioventricular administration, intraperitoneal administration, subcutaneous administration, or intramuscular administration, but the route of administration is not limited thereto. The protein preparation according to the present invention may be used as a pharmaceutical composition.

The composition containing a vector according to the present invention may contain a pharmaceutically acceptable diluent, carrier, or vehicle in addition to a vector. The composition containing a vector according to the present invention can be parenterally administered, for example, through intravenous administration, intracavitary administration, intracardioventricular administration, intraperitoneal administration, subcutaneous administration, or intramuscular administration, but the route of administration is not limited thereto. The composition containing a vector according to the present invention may be used as a pharmaceutical composition.

In another aspect of the present invention, the present invention provides a method for treating a senescence-related condition in a subject being senescent or suspected to be senescent, the method including administrating GDF6 protein, a cell secreting GDF6 protein, a vector for expression of GDF6 to be used in the present invention to a subject in need thereof.

Provided in a certain embodiment of the present invention is a method for treating a senescence-related condition in a subject being senescent or suspected to be senescent, the method including administrating a miR-17 family member, a vector for expression of the miR-17 family member, or a cell overexpressing the miR-17 family member to be used in the present invention to a subject in need thereof.

Candidate compounds for use in treating a senescence-related condition can be screened through a procedure in which a cell expressing GDF6 or a miR-17 family member and a test compound are brought into contact, the change in the amount of expression of GDF6 and/or the amount of secretion of GDF6 protein after the contact is detected, and a compound which enhances expression of GDF6 and/or secretion of GDF6 protein is selected.

"Test compound" to be used for screening is not limited, and examples of the test compound include expression products from gene libraries, synthesized low-molecular-weight compound libraries, peptide libraries, antibodies, substances released from bacteria, extract solution or purified or partially purified polypeptides from and culture supernatant for cells (microorganisms, plant cells, and animal cells), extracts derived from marine organisms, extracts derived from a plant or animal, soils, and random phage peptide display libraries.

"Contact" between the cell expressing GDF6 and the test compound can be achieved, for example, through adding the test compound into a medium in which the cell expressing GDF6 or a miR-17 family member is cultured and maintained.

The detection of the change in the amount of expression of GDF6 and/or the amount of secretion of GDF6 protein after the contact with the test compound can be performed by using a method known to those skilled in the art. Examples of the detection method include an RT-PCR method to measure the amount of RNA in GDF6 and immunoprecipitation to be performed by using culture supernatant collected.

Examples demonstrated in the following are examples for description of the present invention, and are not intended to limit the technical scope of the present invention. The technical scope of the present invention is defined by the description in the claims.

EXAMPLES

Example 1: Senescence of Mesenchymal Stem/Stromal Cell (MSC) and Change in Gene Expression In this Example, the variation of gene expression in association with senescence of MSCs was analyzed.

Primary MSCs were CD45-negative, CD31-negative, TER119-negative, Pdgfra-positive and Sca-1-positive, and prepared from a C57BL/6JJc1 mouse by using a conventional method (see Morisawa S et al., J Exp. Med., 206: 2483-2496, 2009). MSCs prepared from a 2- to 3-week-old mouse were used as Young MSCs, and MSCs prepared from a 18-month-old or older mouse were used as Old MSCs (herein, also referred to as "young-aged MSCs" and "old-aged MSCs", respectively). Culture of MSCs was performed in an alpha-modified minimum essential medium (α-MEM) by using an incubator at 37° C. and 5% $CO_2$.

Osteogenic differentiation and adipogenic differentiation were elicited by using a Human Mesenchymal Stem Cell Osteogenic/Adipogenic Differentiation BulletKit Medium (manufactured by Lonza) in accordance with the manual from the manufacturer. Detection of osteoblasts was performed by using a Leukocyte Alkaline Phosphatase Kit (manufactured by Sigma-Aldrich Co. LLC.), and detection of adipocytes was performed in accordance with a conventional method through detection of oil droplets produced by adipocytes with Oil Red O (MUTO PURE CHEMICALS CO., LTD., 40491).

As reported previously, each Young MSC was retaining satisfactory multipotency to differentiate into an osteoblast, an adipocyte, a chondrocyte, a myoblast, and a nerve. In contrast, the osteogenic potency and adipogenic potency of each Old MSC had been lowered (FIG. 1a). As shown by the graph in the left side of FIG. 1a, the area of ALP-positive cells for the Old MSCs was as small as approximately 20% of that for the Young MSCs. This result revealed that the potency of differentiation of an MSC into an adipocyte is lowered in association with senescence. As shown by the graph in the right side of FIG. 1a, the area of Oil Red O-positive cells for the Old MSCs was as small as half or less of that for the Young MSCs. This result revealed that the potency of osteogenic differentiation of an MSC is lowered in association with senescence. The experiment was repeated three times. Any of the results exhibited a statistically significant difference ($p<0.05$).

Increase in expression of Senescence-Associated Secretory Phenotype (SASP)-like inflammatory factors was found for the Old MSCs, and the expression level varied with respect to some growth factors (FIGS. 1b and 1c).

Example 2: Identification of Factors Relating to Senescence of MSC

In this Example, an attempt was made to identify factors relating to the deterioration of the potency of an MSC in association with senescence as demonstrated in Example 1.

For this purpose, RNA was extracted from Old MSCs and Young MSCs, and change in expression of mRNA and miRNA relating to cellular senescence was analyzed by using a microarray (SurePrint G3 Mouse GE microarray manufactured by Agilent Technologies) and an miRNA qPCR array (TaqMan Array Rodent MicroRNA A+B Cards Set v3.0 manufactured by Thermo Fisher Scientific Inc., under the brand of Applied Biosystems). Differentiation was measured by using a Hybrid Cell Count program and BZ-X700 microscope (manufactured by KEYENCE CORPORATION), and ImageJ software (http://imagej.nih.gov/ij/).

The analysis found that expression was lowered in relation to senescence for all of the miR-17 family members (FIG. 2a).

miR-17 has been reported to promote the differentiation of an MSC into an osteoblast on the one hand, and reported to suppress it on the other hand, and the role for the potency of differentiation of an undifferentiated MSC is still unclear. In view of this, miR-17 (SEQ ID NO: 4) was introduced into MSCs by using lentiviruses, and the MSCs were cultured for 1 week, and the potency of differentiation was evaluated. The lentiviruses were produced by using a conventional method (Naka-Kaneda H., PNAS, 111:1604-1609, 2014). Lentiviruses including miR-LacZ incorporated therein were used as a negative control.

The potency of differentiation of an MSC into an osteoblast was evaluated through measurement of the ALP-positive area. The potency of differentiation of an MSC into an adipocyte was evaluated through measurement of the Oil Red O-positive area. The osteogenic potency and adipogenic potency were partially recovered for Old MSCs with over-expression of miR-17 (FIGS. 2b and 2c). The ALP-positive area for the cells with introduction of miR-17 was approximately 1.6 times larger than that for the negative control, and the Oil Red O-positive area for the cells with introduction of miR-17 was approximately 1.7 times larger than that for the negative control (the graphs in FIGS. 2b and 2c).

Example 3: Transplantation Experiment for Old MSCs with Overexpression of miR-17

Example 2 demonstrated that the osteogenic potency and adipogenic potency, which were characteristic of the phenomenon of senescence, were partially recovered for the Old MSCs with overexpression of miR-17. In the present Example, such MSCs whose deteriorated potency associated with senescence had been recovered were transplanted, and the influence of the MSCs on the regenerative ability of the recipient for the lymphocytes was examined.

Figure 3:
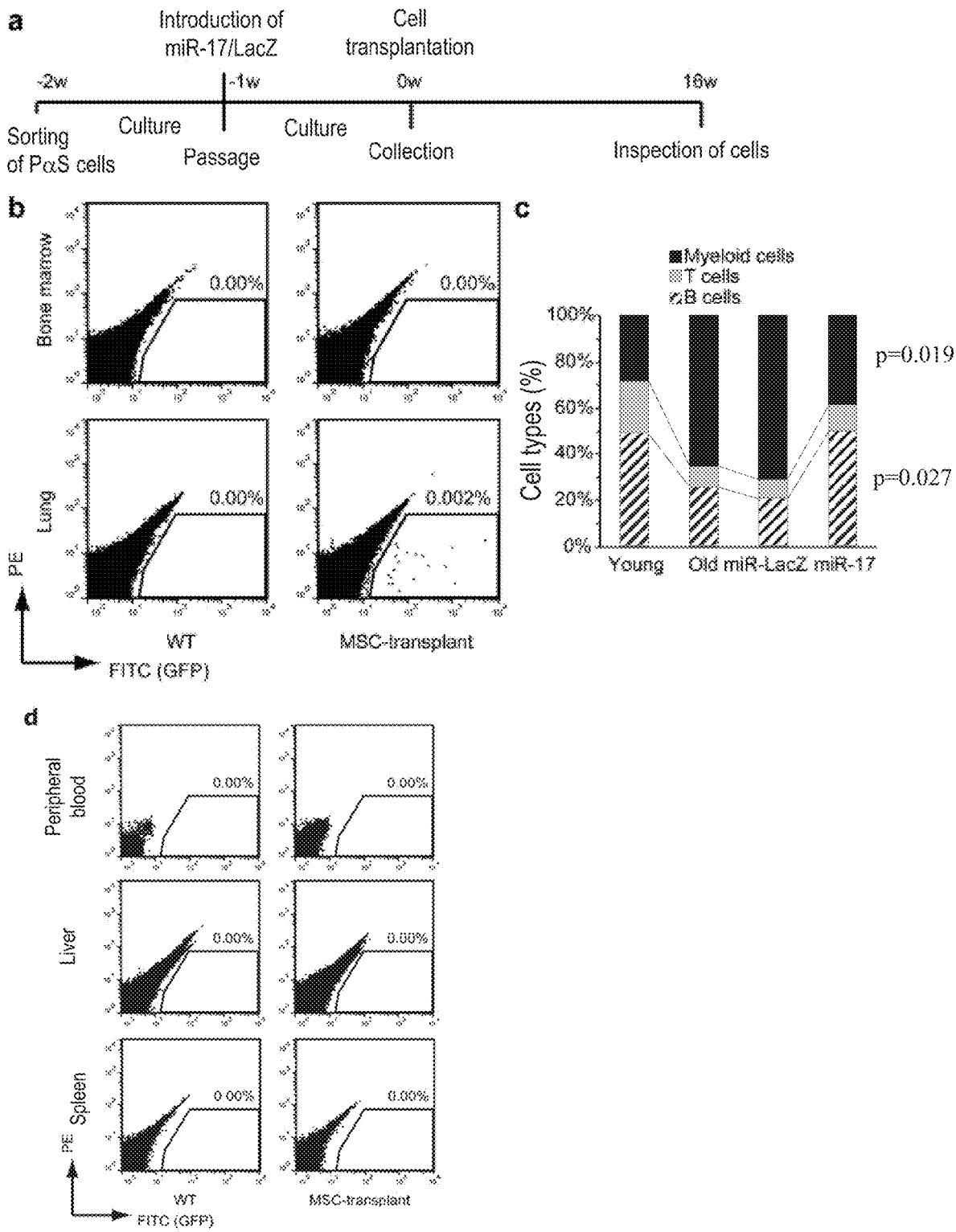
FIG. 3 illustrates a scheme to administer old MSCs with introduction of miR-17 to an old mouse (FIG. 3a), and shows engraftment of the cells administered into different tissues (FIGS. 3b and 3d) and change in the number of lymphocytes in the mouse after the administration (FIG. 3c).

A transplantation experiment was conducted in accordance with a scheme illustrated in FIG. 3a. Specifically, MSCs were prepared as PαS cells (PDGFRα+, Sca1+ cells) from an old mouse aged 18 months or older, and the MSCs were overexpressed miR-17 or LacZ together with green fluorescent protein (GFP) by using lentiviruses 1 week after the preparation. Thereafter, the cells were further cultured for 1 week and then collected, and the collected cells were intravenously administered to an old mouse aged 18 months or older. After 16 weeks, the old mouse having been subjected to the transplantation was analyzed.

First, the fractions of B220-positive B-cells, CD3ε-positive T-cells, and CD11b-positive myeloid cells in the peripheral blood were analyzed through FACS.

The analysis showed that the fraction of lymphocytes, which are depleted in association with senescence, in the mouse with transplantation of the Old MSCs with overexpression of miR-17 was significantly recovered (FIG. 3c).

To examine the distribution of the transplanted MSCs in the body, the bone marrow, lung, liver, spleen, and peripheral blood were taken, and the GFP expression was analyzed through FACS. In the analysis, the transplanted MSCs were detected only from the lung (see FIG. 3b). In contrast, the transplanted MSCs were not detected from the bone marrow, liver, spleen, and peripheral blood (FIGS. 3b and 3d).

The results of FIGS. 3b and 3d showed that the transplanted MSCs were present neither in the bone marrow nor in the peripheral blood. However, delay/recovery effect due to transplantation of the MSCs with overexpression of miR-17 on reduction of lymphocytes in association with senescence was observed from the result of FIG. 3c. These results suggest that not the transplanted MSCs themselves but a secretory factor released from the transplanted MSCs with overexpression of miR-17 was responsible for recovery of lymphocytes.

Example 4: Identification of Secretory Factor to Recover Senescence

The results of Example 3 revealed that the MSCs released a secretory factor to recover senescence to exert recovery and/or amelioration effect on deterioration of physiological functions due to aging in the old mouse. In the present Example, an attempt was made to identify a secretory factor responsible for recovery and/or amelioration effect on deterioration of physiological functions due to aging.

The gene expression profiles of Young MSCs, Old MSCs, and old mouse with transplantation of MSCs with overexpression of miR-17 were analyzed by using a microarray as described in Example 2, and intergroup comparison was made. On the basis of criteria for selection of candidate genes as set forth below, 59,305 genes (probes) were narrowed down to 701 genes (probes) (FIG. 4a).

Criteria for Selection of Candidate Genes
(1) The amount of expression in the Old MSCs was less than 0.7 times larger than that in the Young MSCs
(2) The amount of expression in the Old MSCs with introduction of the negative control (miR-LacZ) was less than 0.7 times larger than that in the Young MSCs
(3) The amount of expression in the Old MSCs with overexpression of miR-17 was 0.7 times or more larger than that in the Young MSCs
(4) The amount of expression in the Old MSCs with overexpression of miR-17 was more than 1.5 times larger than that in the Old MSCs with introduction of the negative control The criteria (1) and (2) relate to conditions for decrease in the amount of expression in the Old MSCs, and the criteria (3) and (4) relate to conditions for amelioration of the amount of expression due to overexpression of miR-17.

From the resulting 701 genes, 13 genes (underlined genes in FIG. 4b) were selected each as a gene suspected to be a secretion factor through gene ontology analysis. A secretory factor responsible for recovery and/or amelioration effect on deterioration of physiological functions due to aging was expected to be included in the 13 genes.

Under this expectation, each of the 13 genes was cloned from a cDNA library of a Young MSC and introduced into 293T cells, and the culture supernatant containing a secretion factor produced by each gene was collected, as illustrated in FIG. 4c.

Osteogenic differentiation assay was then performed for the cells by using the collected culture supernatant. The assay performed was according to a scheme illustrated in FIG. 4c. Specifically, bone marrow stromal cells (BMSCs) were collected from the bone marrow of an old mouse aged 18 months or older, and seeded in a culture dish. After the cells were cultured in an MSC-growing medium (α-MEM+ 10% FBS) for 5 days, the cells were reseeded. One day after the seeding, the cells were cultured in an osteoblast differentiation medium (Lonza, PT-3002) containing the collected culture supernatant at 50% or free of the culture supernatant for 14 days.

When the cells collected were stained with ALP, only the Old MSCs cultured in the culture supernatant for the 293T cells with introduction of Gdf6 were ALP-positive (FIG. 4d).

Gdf6 is a secretion factor belonging to the TGF-β superfamily, and known to be necessary for formation of the eyes, skull, a part of bones, and joints of the feet (Asai-Coakwell M, et al., Am. J. Hum. Genet., 80, 306-315, 2007; and Clendenning D. E. & Mortlock D. P., PLoS One, 7, e36789, 2012). Gdf6 is known to utilize BMP receptors which Bmp2/4 utilize (Mazerbourg S, et al., J. Biol. Chem., 280, 32122-32132, 2005). In view of this, an experiment to compare the characteristics of Bmp2/4 and Gdf6 was conducted.

When expression of Bmp2/4 was compared between Young MSCs and Old MSCs, no remarkable difference was observed between the Young MSCs and the Old MSCs (FIG. 4e), and thus it was revealed that expression of Bmp2/4 does not largely vary through cellular senescence. When Bmp2/4 was introduced into Young MSCs and Old MSCs, the Bmp2/4 significantly enhanced osteogenic differentiation in the Young MSCs, and the Bmp2/4 exhibited only a small amelioration effect in the Old MSCs (FIG. 4f). These results suggest that Gdf6 ameliorated the osteogenic potency of the Old MSCs through a pathway independent of those of Bmp2/4.

Example 5: Examination of Gdf6's Physiological Function and Effect on Senescence—Part 1

In the present Example, the physiological meaning of Gdf6 was analyzed by using MSCs through in vitro knock-down of Gdf6. In addition, Gdf6 was expressed in vivo in an old mouse and the effect on the phenomenon of senescence was examined in the present Example.

Knock-down of Gdf6 was examined by using three types of shRNA. The sequences of the shRNAs used were as set forth in SEQ ID NO: 23 (shGdf6-1), SEQ ID NO: 24 (shGdf6-2), and SEQ ID NO: 25 (shGdf6-3). Each shRNA was introduced into Young MSCs by using a conventional method. For a control shRNA, SEQ ID NO: 22 was used.

A vector with cloned Gdf6 to express fused protein including addition of the red fluorescent protein mKate2 at the N-terminus was produced, and co-introduced together with a lentivirus vector including GFP as a reporter incorporated therein for expression of the shRNA into 293T cells, and the 293T cells were analyzed through FACS. The amount of expression of the shRNA was read from the GFP expression intensity and the amount of expression of Gdf6 was read from the mKate2 expression intensity, and the knock-down efficiency was evaluated. Reduction of the number of mKate2-positive cells when shGdf6-1, -2, or -3 was introduced was relatively quantified with reference to the number of mKate2-positive cells when the control shRNA was introduced, and the result confirmed that shGdf6-1 achieved the most effective knock-down.

The area of ALP-positive cells (FIG. 5a) and the area of Oil Red O-positive cells (FIG. 5b) were larger for the case that Gdf6 was knocked down. This result revealed that Gdf6 is involved in both adipogenesis and osteogenesis.

Subsequently, human GDF6 was overexpressed in an old mouse aged 18 months or older, and the effect was examined. The human GDF6 used was GDF6 having a sequence as set forth in SEQ ID NO: 1 (hereinafter, referred to as "hGDF6"). Lentiviruses including a DNA encoding hGDF6 expressibly linked thereto were intraperitoneally injected into a mouse. A mouse without injection and a mouse with expression of EGFP instead of GDF6 were used as negative controls. The lentiviruses were intraperitoneally injected three times every other day.

Figure 6:
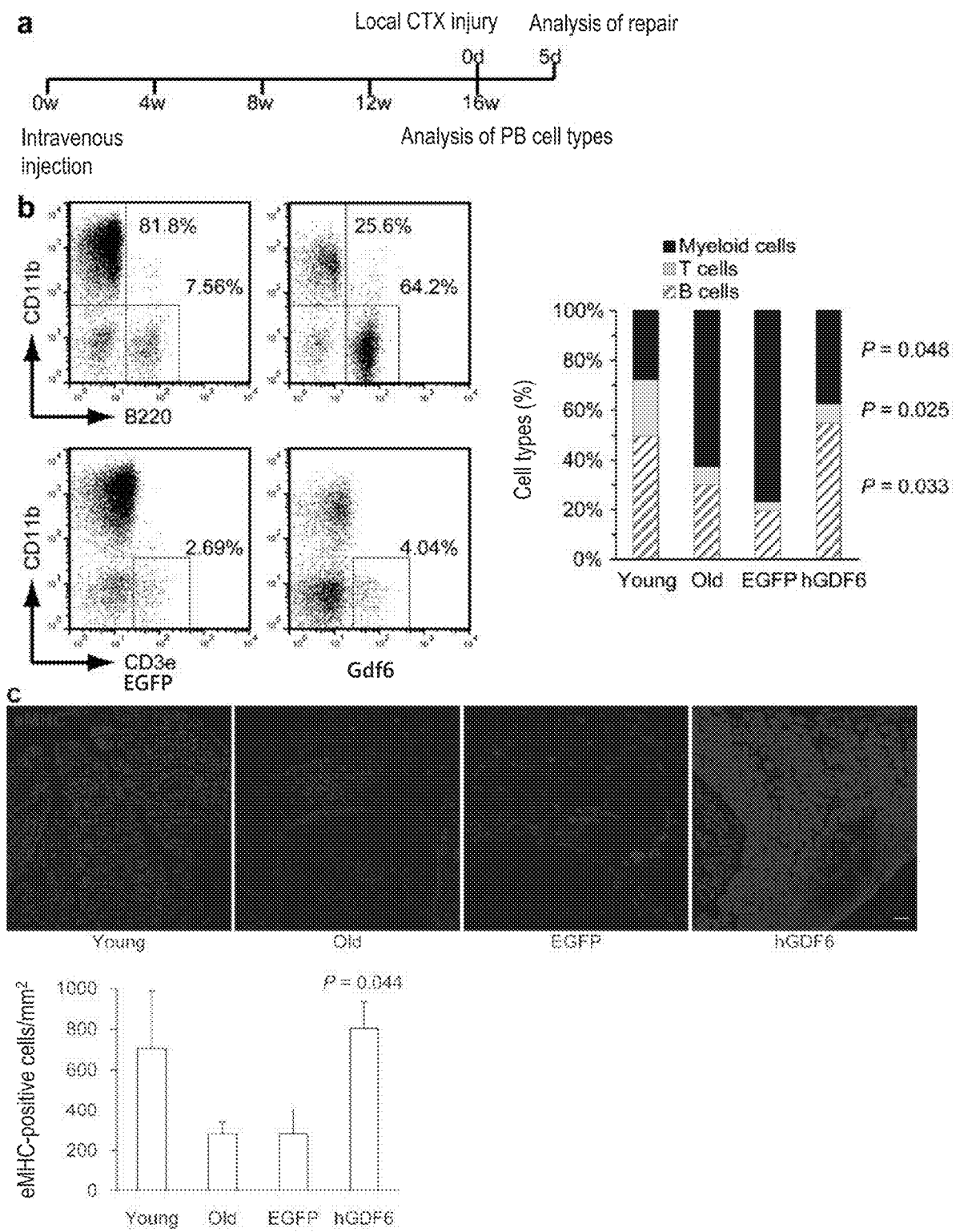
FIG. 6 shows results of an experiment in which GDF6-expressing viruses were intraperitoneally administered to a mouse.

The peripheral blood was collected 4, 8, 12, and 16 weeks after the injection, and the cell type fractions in the peripheral blood were analyzed (FIG. 6a). The result showed that the fractions of B220-positive cells (i.e., B-cells) and CD3e-positive cells, (i.e., T-cells), which are lymphoid cells, were higher and the fraction of CD11b-positive cells (i.e., myeloid cells) was lower for the old mouse with introduction of hGDF6 (FIG. 6b, left dot plots). Introduction of hGDF6 into the old mouse resulted in recovery of the fraction of myeloid cells and the fraction of B-cells each to a level equivalent to that for the young mouse (FIG. 6b, right graph).

Subsequently, the tibialis anterior muscle was injured with local injection of cardiotoxin (CTX) 16 weeks after the injection of the lentiviruses, and repair of the injury was observed 5 days after the local injection (FIG. 6a). Repair was examined through the presence or absence of an embryonic myosin heavy chain-positive (eMHC+) nascent myoblast.

Immunohistological staining was performed as follows: first, the tissue of the injured portion was embedded in paraffin, and eMHC-positive cells were stained with an anti-eMHC antibody (MYH3; 1:50, Santa Cruz Biotechnology Inc., sc-53091), and Sox2-positive cells were stained with an anti-Sox2 antibody (1:100, Abcam, ab92494). Alexa Flour-conjugated anti-mouse and anti-rabbit IgG antibodies (1:500, Thermo Fisher Scientific, A21424, A21206) were used as secondary antibodies. The sections were analyzed by using a BZ-X700 microscope (manufactured by KEYENCE CORPORATION) and accompanying Hybrid Cell Count function.

The results were as shown in FIG. 6c. As can be seen from FIG. 6c, a large number of eMHC-positive myoblasts appeared for the young mouse, and, on the other hand, the number was small for the old mouse and the old mouse with introduction of EGFP. In contrast, a significantly large number of eMHC-positive myoblasts appeared for the old mouse with overexpression of hGDF6 (FIG. 6c). Comparison of the number of eMHC-positive myoblasts per unit area revealed that introduction of hGDF6 provided the old mouse with muscle regeneration at a level equivalent to or higher than that for the young mouse (FIG. 6c).

Figure 10:
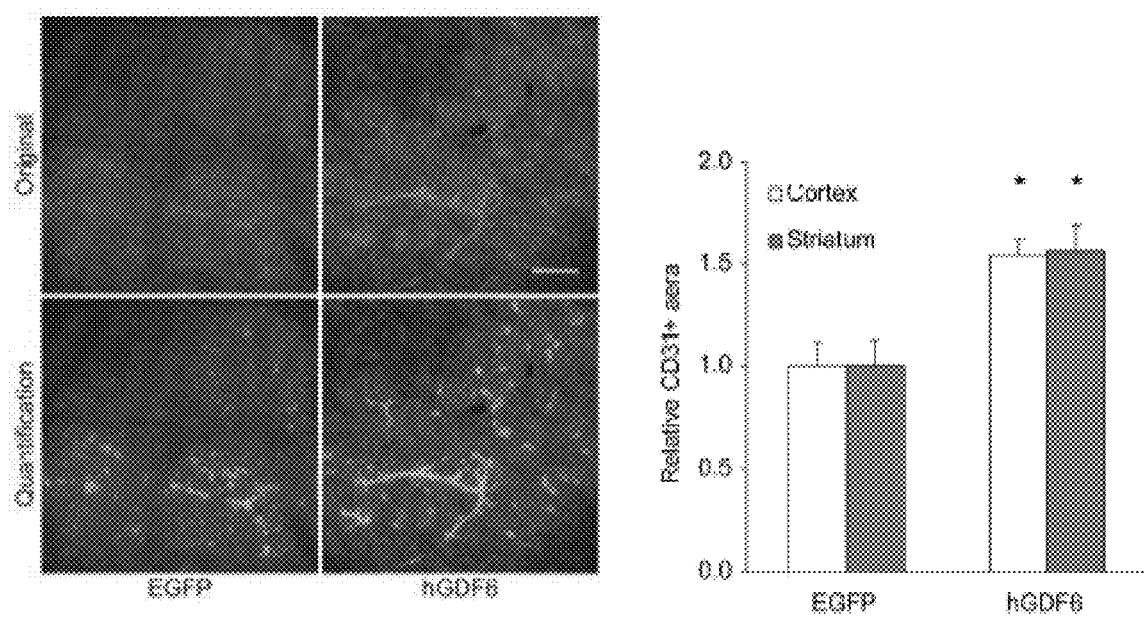
FIG. 10 shows the immuno-histochemical images obtained by using an anti-CD31 antibody in a brain tissue section from an old mouse with overexpression of GDF6 (left).
Figure 11:
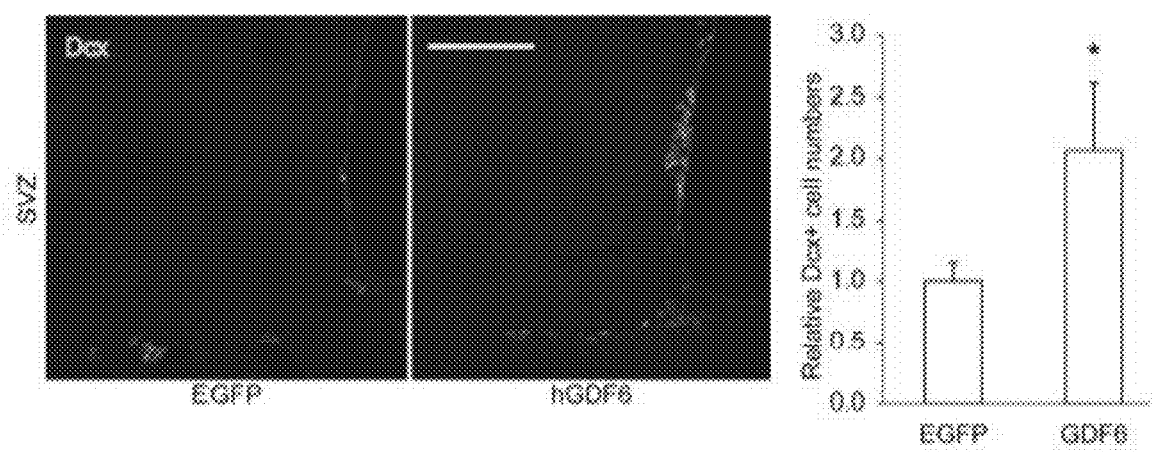
FIG. 11 shows the immuno-histochemical image obtained by using an anti-Dcx antibody in a brain tissue section from an old mouse with overexpression of GDF6 (left).

Further, Sox2-positive neural precursor cells were examined for each mouse 16 weeks after the injection of the lentiviruses. The results showed that the fraction of Sox2-positive cells, which was lower for the old mouse, recovered to a level equivalent to that for the young mouse through overexpression of hGDF6 (FIG. 7a). This recovery of the fraction was found in a wide region including the subventricular zone and the striatum. A brain tissue section from the old mouse was subjected to immunohistological staining with an antibody against CD31 as a vascular endothelial marker, and the results clearly showed that the vascular tissue significantly increased in the brain tissue of the mouse with overexpression of GDF6, as shown in FIG. 10. Further, a brain tissue section from the old mouse was stained with an antibody against Dcx to observe neuroblasts, and the results clearly showed that GDF6 increased the number of neuroblasts to ameliorate the neurogenesis, as shown in FIG. 11.

hGDF6 in the plasma of each mouse was examined through Western blotting. The plasma was purified by using an *Aurum* Serum Protein Mini Kit (Bio-Rad Laboratories, Inc., 7326701), and an anti-GDF6 antibody (Sigma-Aldrich Co. LLC., PRS4691) was used as a detection antibody for Western blotting. From the results, hGDF6 in a full-length form, as the inactive form, and hGDF6 in a dimer form, as the activated form, were found in the plasma over 10 days to 5 months after the injection of the lentiviruses (FIG. 7b).

Example 6: Examination of Gdf6's Physiological Function and Effect on Senescence—Part 2

In the present Example, it was examined whether GDF6 is capable of suppressing secretion of SASP factors in association with cellular senescence.

Lentiviruses encoding hGDF6 were intraperitoneally administered to an old mouse aged 18 months or older to overexpress hGDF6 in the same manner as in Example 5, and the peripheral blood was collected from the old mouse 12 weeks after the injection, and the plasma was collected through centrifugation. The plasma protein levels of inflammatory cytokines or chemokines of IL1-b, IL-6, IL-17, G-SCF, MCP-1 (CCL2), MIP-1a (CCL3), and MIP-1b (CCL4), which are known as SASP factors, were quantified by using a Bio-Plex Pro Mouse Cytokine Assay (Bio-Rad Laboratories, Inc.) and a Bio-Plex200 (Bio-Rad Laboratories, Inc.). The plasma inflammatory cytokine or chemokine levels for a mouse with expression of EGFP, as a subject for comparison, were used as reference values (1), and relative values were determined.

Figure 8:
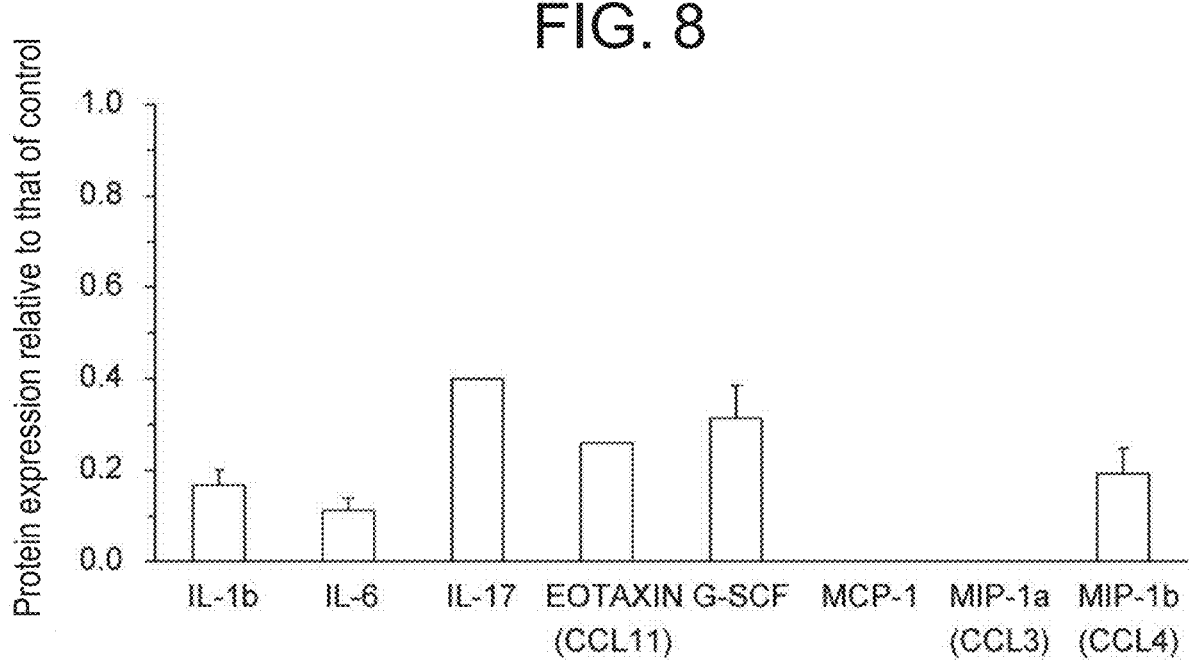
FIG. 8 shows relative values of the amounts of various inflammatory cytokines in the blood of an old mouse to which viruses for overexpression of GDF6 were intraperitoneally administered, using as a standard a value for a mouse to which EGFP-expressing lentiviruses were administered, where the amounts of various inflammatory cytokines were measured by using a Multiplex method.

The results were as shown in FIG. 8. As can be seen from FIG. 8, GDF6 was found to decrease the level of each of the inflammatory cytokines and chemokines as SASP factors to 0.5 or lower (FIG. 8). These results demonstrated that GDF6 suppresses secretion of SASP factors in association with cellular senescence.

Example 7: Examination of Effect of Cell with Introduction of Gdf6 Gene on Senescence In Examples 5 and 6, lentiviruses were administered to an old mouse itself to overexpress GDF6 in the mouse. In the present Example, peripheral blood with overexpression of GDF6 was administered to an old mouse, and the effect on senescence was examined.

From each of 20 young mice, 200 μL of the peripheral blood was taken, and the leukocyte fraction was obtained through hemolysis of erythrocytes. The lentiviruses for expression of hGDF6 in aforementioned Examples were introduced into half of the leukocyte fraction, and lentiviruses for expression of EGFP (control) were introduced into the other half, and the resultants were cultured for 3 hours. Expression of hGDF6 or EGFP by the lentiviruses was confirmed, and sufficient secretion of hGDF6 was confirmed from the culture supernatant. After the culturing, a group of GDF6-expressing cells or a group of EGFP-expressing cells, each group consisting of fifty million to two hundred million cells in total, was transplanted into an old mouse through intravenous administration. After 4 weeks, the peripheral blood was collected from each of the old mice to which each of the cell groups had been administered, and the fraction of lymphocytes among cell types in the peripheral blood was analyzed in the same manner as in Example 5.

Figure 9:
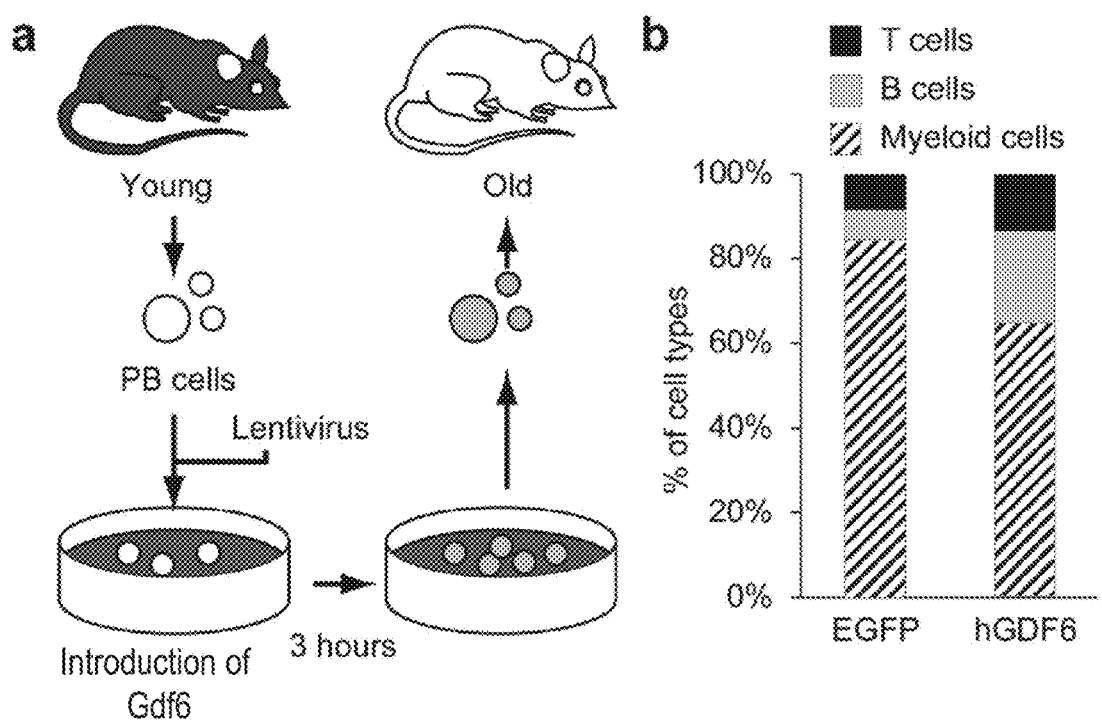
FIG. 9 shows the ratio of lymphocytes after cells having the introduced Gdf6 gene were administered to an old mouse.

The results were as shown in FIG. 9. As can be seen from FIG. 9, the fractions of B220-positive cells (i.e., B-cells) and CD3e-positive cells, (i.e., T-cells), which are lymphoid cells, were higher and the fraction of CD11b-positive cells (i.e., myeloid cells) was lower for the old mouse with introduction of the hGDF6-expressing cell group.

These results confirmed that the effect obtained through introduction of a vector for expression of a gene for hGDF6 is obtained through administration of cells overexpressing hGDF6 to an old mouse.

Above-described Examples revealed that MSCs exert recovery and/or amelioration effect on deterioration of physiological functions due to aging in an old mouse through overexpression of miR-17, that the action is exerted via a secretion factor, and that GDF6 as a secretion factor is responsible for the recovery and/or amelioration effect on deterioration of physiological functions due to aging. Specifically, GDF6 present in plasma was capable of suppressing/recovering reduction of lymphocytes, deterioration of regenerative ability against muscle injury, reduction of neural precursor cells, and secretion of inflammatory cytokines and chemokines in association with senescence. In addition, hair glossiness recovered in an old mouse with overexpression of GDF6. Thus, GDF6 was revealed to be applicable to treatment of various conditions associated with senescence.

Example 8: Examination of Effect of Gdf6 on Hair

Figure 12:
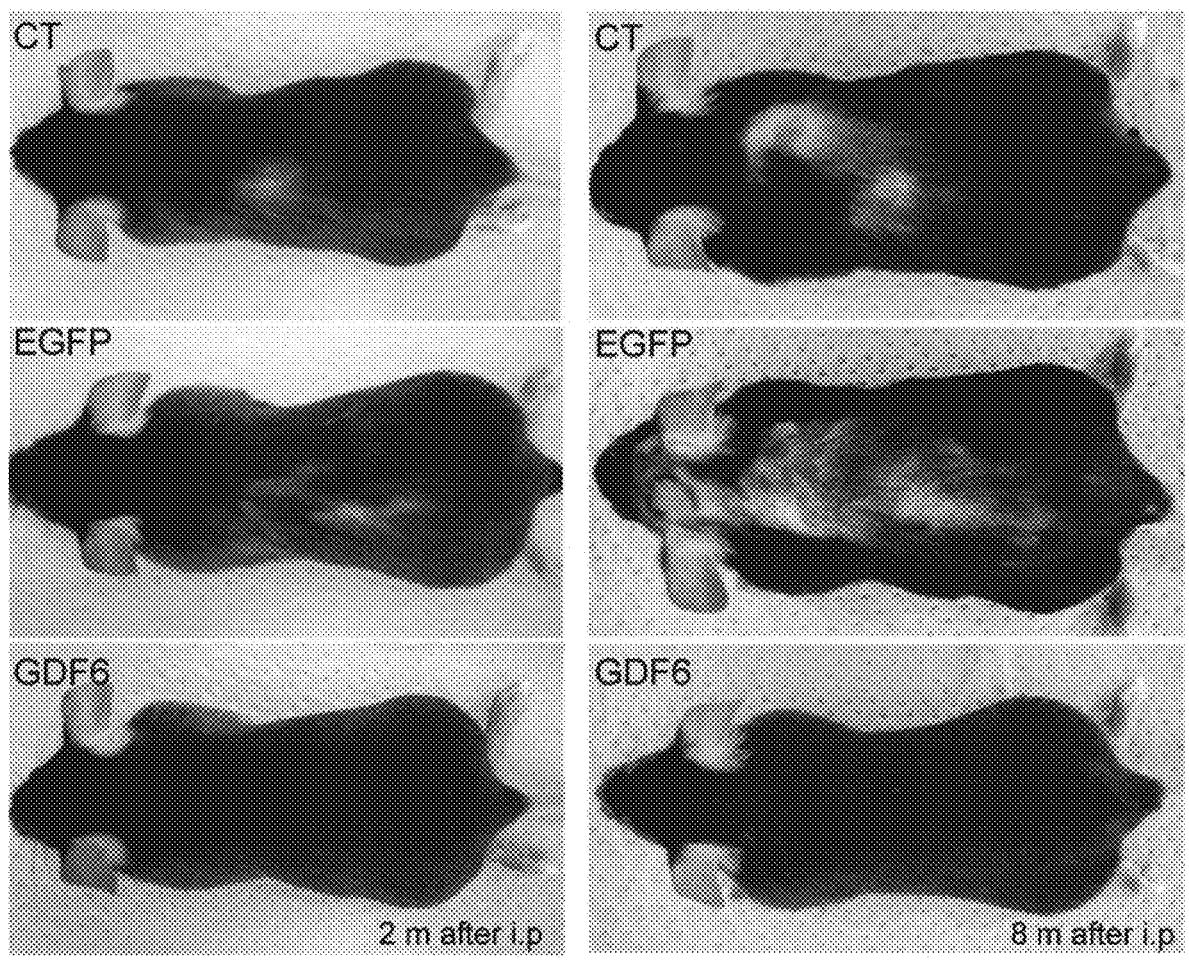
FIG. 12 shows the result that GDF6 recovered loss of hair and deterioration of hair glossiness in a young mouse, where "GDF6" shows a result for a mouse to which lentiviruses including a DNA encoding hGDF6 expressively linked thereto were administered, "CT" shows a result for a negative control without virus administration, "EGFP" shows a result for a negative control with expression of EGFP instead of GDF6, photographs in the left side show results 2 months after the administration, and photographs in the right side show results 8 months after the administration.

Next, the lentiviruses including a DNA encoding hGDF6 expressibly linked thereto in aforementioned Example were intraperitoneally administered to a young mouse at a frequency of once per day for consecutive 3 days, and the young mouse was followed up for loss of hair and deterioration of hair glossiness in association with senescence. A mouse without virus administration and a mouse with expression of EGFP instead of GDF6 for use as negative controls were grown in the same cage. The results were as shown in FIG. 12. As can be seen from FIG. 12, the hair and hair glossiness in the whole back of the mouse with expression of hGDF6 were maintained both 2 months and 8 months after the administration, in contrast to the negative controls.

The invention claimed is:

1. A method of treating a human subject having a deterioration, comprising administering to the subject
an effective amount of GDF6 protein;
such that the treatment will recover and/or ameliorate the deterioration in the subject,
wherein the deterioration has been caused by aging and is selected from the group consisting of reduction of lymphocytes, deterioration of the capability to produce lymphocytes, reduction of differentiation of mesenchymal stem cells (MSCs) into adipocytes, reduction of osteogenic differentiation of MSCs, reduction of nerve cells, reduction of production ability of embryonic myosin heavy chain (eMHC) positive nascent muscle cells, reduction of production ability of neuroblasts, and reduction or loss of Sox2-positive neural precursor cells.

2. The method according to claim 1, wherein the GDF6 protein has:
   (i) the amino acid sequence as set forth in SEQ ID NO: 2 or 3;
   (ii) a sequence having 90% or higher homology with the amino acid sequence as set forth in SEQ ID NO: 2 or 3;
   (iii) an amino acid sequence obtained by providing the amino acid sequence as set forth in SEQ ID NO: 2 or 3 with deletion, insertion, and/or substitution of 1 to 10 amino acids; or
   (iv) an amino acid sequence encoded by a sequence hybridizable with a nucleic acid having a sequence complementary to a DNA sequence encoding the amino acid sequence as set forth in SEQ ID NO: 2 or 3 under stringent conditions.

3. The method according to claim 1, wherein the administration is conducted intravenously.

4. The method according to claim 1, wherein the administration is conducted intraperitoneally.

5. The method according to claim 3, wherein the administration is conducted intracerebroventricularly.

6. The method according to claim 1, wherein the deterioration is reduction or loss of Sox2-positive neural precursor cells, and the administration is conducted intracerebroventricularly, wherein the administration increases the Sox2-positive neural precursor cells to promote neurogenesis in the subject.

7. The method according to claim 1, wherein the deterioration is selected from the group consisting of muscle reduction and lowering of resilience to muscle injury, and the administration is conducted intramuscularly, wherein the administration increases the number of embryonic myosin heavy chain (eMHC) positive nascent muscle cells to promote regeneration of the muscle.

8. The method according to claim 1, wherein the human subject is a human subject whose age is over 60.

9. The method according to claim 1, wherein the subject has a reduced GDF6 expression.

10. The method according to claim 9, wherein the treatment will recover the reduced GDF6 expression in the subject.

\* \* \* \* \*

SEQUENCE LISTING

```
<160> NUMBER OF SEQ ID NOS: 25

<210> SEQ ID NO 1
<211> LENGTH: 3716
<212> TYPE: DNA
<213> ORGANISM: Homo sapiens
<220> FEATURE:
<221> NAME/KEY: CDS
<222> LOCATION: (101)..(1468)

<400> SEQUENCE: 1
cccgaggagc cgggccccgg ccgctgtcca gccgctccgt gccccgcgcg tcctgcgccg      60
ccgccaccgc ctcctgggga gacgcagcca cttgcccgcc atg gat act ccc agg     115
                                             Met Asp Thr Pro Arg
                                             1               5 gtc ctg ctc tcg gcc gtc ttc ctc atc agt ttt ctg tgg gat ttg ccc     163
Val Leu Leu Ser Ala Val Phe Leu Ile Ser Phe Leu Trp Asp Leu Pro
                10                  15                  20 ggt ttc cag cag gct tcc atc tca tcc tcc tcg tcg tcc gcc gag ctg     211
Gly Phe Gln Gln Ala Ser Ile Ser Ser Ser Ser Ser Ala Glu Leu
            25                  30                  35 ggt tcc acc aag ggc atg cga agc cgc aag gaa ggc aag atg cag cgg     259
Gly Ser Thr Lys Gly Met Arg Ser Arg Lys Glu Gly Lys Met Gln Arg
        40                  45                  50 gcg ccg cgc gac agt gac gcg ggc cgg gag ggc cag gaa cca cag ccg     307
Ala Pro Arg Asp Ser Asp Ala Gly Arg Glu Gly Gln Glu Pro Gln Pro
    55                  60                  65 cgg cct cag gac gaa ccc cgg gct cag cag ccc cgg gcg cag gag ccg     355
Arg Pro Gln Asp Glu Pro Arg Ala Gln Gln Pro Arg Ala Gln Glu Pro
70                  75                  80                  85 cca ggc agg ggt ccg cgc gtg gtg ccc cac gag tac atg ctg tca atc     403
Pro Gly Arg Gly Pro Arg Val Val Pro His Glu Tyr Met Leu Ser Ile
                90                  95                 100
```

-continued

| | | |
|---|---|---|
| tac agg act tac tcc atc gct gag aag ctg ggc atc aat gcc agc ttt<br>Tyr Arg Thr Tyr Ser Ile Ala Glu Lys Leu Gly Ile Asn Ala Ser Phe<br>105 110 115 | | 451 |
| ttc cag tct tcc aag tcg gct aat acg atc acc agc ttt gta gac agg<br>Phe Gln Ser Ser Lys Ser Ala Asn Thr Ile Thr Ser Phe Val Asp Arg<br>120 125 130 | | 499 |
| gga cta gac gat ctc tcg cac act cct ctc cgg aga cag aag tat ttg<br>Gly Leu Asp Asp Leu Ser His Thr Pro Leu Arg Arg Gln Lys Tyr Leu<br>135 140 145 | | 547 |
| ttt gat gtg tcc atg ctc tca gac aaa gaa gag ctg gtg ggc gcg gag<br>Phe Asp Val Ser Met Leu Ser Asp Lys Glu Glu Leu Val Gly Ala Glu<br>150 155 160 165 | | 595 |
| ctg cgg ctc ttt cgc cag gcg ccc tca gcg ccc tgg ggg cca cca gcc<br>Leu Arg Leu Phe Arg Gln Ala Pro Ser Ala Pro Trp Gly Pro Pro Ala<br>170 175 180 | | 643 |
| ggg ccg ctc cac gtg cag ctc ttc cct tgc ctt tcg ccc cta ctg ctg<br>Gly Pro Leu His Val Gln Leu Phe Pro Cys Leu Ser Pro Leu Leu Leu<br>185 190 195 | | 691 |
| gac gcg cgg acc ctg gac ccg cag ggg gcg ccg ccg gcc ggc tgg gaa<br>Asp Ala Arg Thr Leu Asp Pro Gln Gly Ala Pro Pro Ala Gly Trp Glu<br>200 205 210 | | 739 |
| gtc ttc gac gtg tgg cag ggc ctg cgc cac cag ccc tgg aag cag ctg<br>Val Phe Asp Val Trp Gln Gly Leu Arg His Gln Pro Trp Lys Gln Leu<br>215 220 225 | | 787 |
| tgc ttg gag ctg cgg gcc gca tgg ggc gag ctg gac gcc ggg gag gcc<br>Cys Leu Glu Leu Arg Ala Ala Trp Gly Glu Leu Asp Ala Gly Glu Ala<br>230 235 240 245 | | 835 |
| gag gcg cgc gcg cgg gga ccc cag caa ccg ccg ccc ccg gac ctg cgg<br>Glu Ala Arg Ala Arg Gly Pro Gln Gln Pro Pro Pro Pro Asp Leu Arg<br>250 255 260 | | 883 |
| agt ctg ggc ttc ggc cgg agg gtg cgg cct ccc cag gag cgg gcc ctg<br>Ser Leu Gly Phe Gly Arg Arg Val Arg Pro Pro Gln Glu Arg Ala Leu<br>265 270 275 | | 931 |
| ctg gtg gta ttc acc aga tcc cag cgc aag aac ctg ttc gca gag atg<br>Leu Val Val Phe Thr Arg Ser Gln Arg Lys Asn Leu Phe Ala Glu Met<br>280 285 290 | | 979 |
| cgc gag cag ctg ggc tcg gcc gag gct gcg ggc ccg ggc gcg ggc gcc<br>Arg Glu Gln Leu Gly Ser Ala Glu Ala Ala Gly Pro Gly Ala Gly Ala<br>295 300 305 | | 1027 |
| gag ggg tcg tgg ccg ccg ccg tcg ggc gcc ccg gat gcc agg cct tgg<br>Glu Gly Ser Trp Pro Pro Pro Ser Gly Ala Pro Asp Ala Arg Pro Trp<br>310 315 320 325 | | 1075 |
| ctg ccc tcg ccc ggc cgc cgg cgg cgc acg gcc ttc gcc agt cgc<br>Leu Pro Ser Pro Gly Arg Arg Arg Arg Thr Ala Phe Ala Ser Arg<br>330 335 340 | | 1123 |
| cat ggc aag cgg cac ggc aag aag tcc agg cta cgc tgc agc aag aag<br>His Gly Lys Arg His Gly Lys Lys Ser Arg Leu Arg Cys Ser Lys Lys<br>345 350 355 | | 1171 |
| ccc ctg cac gtg aac ttc aag gag ctg ggc tgg gac gac tgg att atc<br>Pro Leu His Val Asn Phe Lys Glu Leu Gly Trp Asp Asp Trp Ile Ile<br>360 365 370 | | 1219 |
| gcg ccc ctg gag tac gag gcc tat cac tgc gag ggt gta tgc gac ttc<br>Ala Pro Leu Glu Tyr Glu Ala Tyr His Cys Glu Gly Val Cys Asp Phe<br>375 380 385 | | 1267 |
| ccg ctg cgc tcg cac ctg gag ccc acc aac cac gcc atc atc cag acg<br>Pro Leu Arg Ser His Leu Glu Pro Thr Asn His Ala Ile Ile Gln Thr<br>390 395 400 405 | | 1315 |
| ctg atg aac tcc atg gac ccc ggc tcc acc ccg ccc agc tgc tgc gtg<br>Leu Met Asn Ser Met Asp Pro Gly Ser Thr Pro Pro Ser Cys Cys Val<br>410 415 420 | | 1363 |

```
ccc acc aaa ttg act ccc atc agc att cta tac atc gac gcg ggc aat     1411
Pro Thr Lys Leu Thr Pro Ile Ser Ile Leu Tyr Ile Asp Ala Gly Asn
            425                 430                 435 aat gtg gtc tac aag cag tac gag gac atg gtg gtg gag tcg tgc ggc     1459
Asn Val Val Tyr Lys Gln Tyr Glu Asp Met Val Val Glu Ser Cys Gly
            440                 445                 450 tgc agg tag cggtgccttt cccgccgcct tggcccggaa ccaaggtggg             1508
Cys Arg
    455 ccaaggtccg ccttgcaggg gaggcctggc tgcagagagg cggaggagga agctggcgct   1568 gggggaggct gagggtgagg gaacagcctg gatgtgagag ccggtgggag agaagggagc   1628 gcagccttcc cagtaacttc tacctgccag cccagaggga aatatggatt ttcacacctt   1688 gcctggccac cctggaaaaa caagccaagg aggatttctt ttgttctgtt ttctctctct   1748 ctctctctct ctctctctct ctctctctct ctctctctat tactgtggct ttggatttcc   1808 ttatgtgtct tacaggcttt gatagaaggg gaggggagga gagatgcata cccgtttctc   1868 aactgctcca tggattgaaa aaataacagt ttaaaaaggg aaacaatgtg ggaggaagaa   1928 tcaccgttga cgcatcttga tttggttggt ttttacatgt gtaaagaagg tggggtctct   1988 ggccatgtca tagcccatgt cttgtgccct cccacacaga aagtgttaga tagggaaatt   2048 ggcaaaaaga atagttaagt caggaatggt cctgcctata aagagccttt gagagaggtg   2108 ggcccacggg tgcccctctc acccatttgt gtactctgtg agtttaccag ctctgccctg   2168 gcctctttcg gtaccaggaa ctggcaacct tcatctcact cctgagggcc aggtctctg    2228 ccttcattgt tgcttttttct ggtgggggca aggggagctg gtatgatgg aatgacaaga   2288 attagtccaa atggaacccc ttgaaggata atgagaaacc acaaggcctg cctctgactg   2348 gggctgacac ggaggtgcat tagcccaggc tggaggtagc ccacccaaat gcccttttctg  2408 attctaattg atttctttca acagaatttg ccaaaattca gacatgcact tctaagggga   2468 aggtgatttt ccagttcaaa aaaatgggca ggagtgggga acaaaacaat taacgtaaga   2528 gctacaaagg agggaaaagg aaccaagaag tagaaggagt cccatcagga gggaagatgg   2588 tgggcctcag ggaggatggg gatcaaggga caggccagga gccaggagtg gggaagggag   2648 ggatgaaagg ggacacaagt ccctgtctct gaagtttctt taaaatctga gttccctccc   2708 ctctctttga cattcctgaa agattaccag ccagcaatag cccagggctc ccccaaaaga   2768 attggttcag attgtaatta tcagttaggc aatgttttta aaacttagta atgagaaact   2828 gtgaaaagag ccaagtgtta cattgagctt ggggtgggag atggggaaca ggcagtgagg   2888 aaggagacag gggtggaatt cgtcttctgg gaggaagctg agagagcac agtgaaattg    2948 aaatacccat tcccagatag tcaaaaacat gaactttccc ccagcctgca ccagtattgt   3008 tttcaaacat tgcccatgag taggcccttt gaagagttag cttcctcctc atctttgact   3068 ataaaattgt ttaatcaatg gaatttgtac cagccttta aaaagtttta gtttttccta    3128 agtgattttg ctctcttcca atctaaacct gttgcttgtt tggttcagag aactacaaac   3188 tgtcaaagaa agggtgggga tgataagaaa tgctaatata aaaatgctaa gtgaaaaaaa   3248 gacttggcca ggagaaataa tttaaaatgc acatttgctt tggatgcact gttgttctgt   3308 taaggctgta tatatttgtt tatttaaggt gactgaaagt gcaaagagga aatggacagc   3368 atgcaattca tcctaatgta caaaacgtta tatgcactca aatgttataa tttctaatat   3428 ttttaaagtt tatattcgag ttgtacaaag ttaagcatta atcagatatt tcattttttc   3488 ataatgttac catttcctta aatattatta caaaatttta agtctgtcta atggagagtt   3548
```

```
tttttttaaac tgtctacctc atataataca agtatttaca acgctaaagt taccagaggt    3608
caatgaataa tcaaaacatt ttttacagta cacctttcct ggatgatatg caatcgaatg    3668
ctatattatt aaacgcattt ttctccttaa taaaaaaaaa aaaaaaaa                 3716
```

<210> SEQ ID NO 2
<211> LENGTH: 455
<212> TYPE: PRT
<213> ORGANISM: Homo sapiens

<400> SEQUENCE: 2

```
Met Asp Thr Pro Arg Val Leu Leu Ser Ala Val Phe Leu Ile Ser Phe
1               5                   10                  15

Leu Trp Asp Leu Pro Gly Phe Gln Gln Ala Ser Ile Ser Ser Ser Ser
                20                  25                  30

Ser Ser Ala Glu Leu Gly Ser Thr Lys Gly Met Arg Ser Arg Lys Glu
            35                  40                  45

Gly Lys Met Gln Arg Ala Pro Arg Asp Ser Asp Ala Gly Arg Glu Gly
        50                  55                  60

Gln Glu Pro Gln Pro Arg Pro Gln Asp Glu Pro Arg Ala Gln Gln Pro
65                  70                  75                  80

Arg Ala Gln Glu Pro Pro Gly Arg Gly Pro Arg Val Val Pro His Glu
                85                  90                  95

Tyr Met Leu Ser Ile Tyr Arg Thr Tyr Ser Ile Ala Glu Lys Leu Gly
            100                 105                 110

Ile Asn Ala Ser Phe Phe Gln Ser Ser Lys Ser Ala Asn Thr Ile Thr
        115                 120                 125

Ser Phe Val Asp Arg Gly Leu Asp Asp Leu Ser His Thr Pro Leu Arg
130                 135                 140

Arg Gln Lys Tyr Leu Phe Asp Val Ser Met Leu Ser Asp Lys Glu Glu
145                 150                 155                 160

Leu Val Gly Ala Glu Leu Arg Leu Phe Arg Gln Ala Pro Ser Ala Pro
                165                 170                 175

Trp Gly Pro Pro Ala Gly Pro Leu His Val Gln Leu Phe Pro Cys Leu
            180                 185                 190

Ser Pro Leu Leu Leu Asp Ala Arg Thr Leu Asp Pro Gln Gly Ala Pro
        195                 200                 205

Pro Ala Gly Trp Glu Val Phe Asp Val Trp Gln Gly Leu Arg His Gln
210                 215                 220

Pro Trp Lys Gln Leu Cys Leu Glu Leu Arg Ala Ala Trp Gly Glu Leu
225                 230                 235                 240

Asp Ala Gly Glu Ala Glu Ala Arg Ala Arg Gly Pro Gln Gln Pro Pro
                245                 250                 255

Pro Pro Asp Leu Arg Ser Leu Gly Phe Gly Arg Arg Val Arg Pro Pro
            260                 265                 270

Gln Glu Arg Ala Leu Leu Val Val Phe Thr Arg Ser Gln Arg Lys Asn
        275                 280                 285

Leu Phe Ala Glu Met Arg Glu Gln Leu Gly Ser Ala Glu Ala Ala Gly
290                 295                 300

Pro Gly Ala Gly Ala Glu Gly Ser Trp Pro Pro Ser Gly Ala Pro
305                 310                 315                 320

Asp Ala Arg Pro Trp Leu Pro Ser Pro Gly Arg Arg Arg Arg Thr
                325                 330                 335

Ala Phe Ala Ser Arg His Gly Lys Arg His Gly Lys Lys Ser Arg Leu
            340                 345                 350
```

```
Arg Cys Ser Lys Lys Pro Leu His Val Asn Phe Lys Glu Leu Gly Trp
            355                 360                 365

Asp Asp Trp Ile Ile Ala Pro Leu Glu Tyr Glu Ala Tyr His Cys Glu
        370                 375                 380

Gly Val Cys Asp Phe Pro Leu Arg Ser His Leu Glu Pro Thr Asn His
385                 390                 395                 400

Ala Ile Ile Gln Thr Leu Met Asn Ser Met Asp Pro Gly Ser Thr Pro
                405                 410                 415

Pro Ser Cys Cys Val Pro Thr Lys Leu Thr Pro Ile Ser Ile Leu Tyr
            420                 425                 430

Ile Asp Ala Gly Asn Asn Val Val Tyr Lys Gln Tyr Glu Asp Met Val
        435                 440                 445

Val Glu Ser Cys Gly Cys Arg
    450                 455

<210> SEQ ID NO 3
<211> LENGTH: 120
<212> TYPE: PRT
<213> ORGANISM: Homo sapiens

<400> SEQUENCE: 3

Thr Ala Phe Ala Ser Arg His Gly Lys Arg His Gly Lys Lys Ser Arg
1               5                   10                  15

Leu Arg Cys Ser Lys Lys Pro Leu His Val Asn Phe Lys Glu Leu Gly
            20                  25                  30

Trp Asp Asp Trp Ile Ile Ala Pro Leu Glu Tyr Glu Ala Tyr His Cys
        35                  40                  45

Glu Gly Val Cys Asp Phe Pro Leu Arg Ser His Leu Glu Pro Thr Asn
    50                  55                  60

His Ala Ile Ile Gln Thr Leu Met Asn Ser Met Asp Pro Gly Ser Thr
65                  70                  75                  80

Pro Pro Ser Cys Cys Val Pro Thr Lys Leu Thr Pro Ile Ser Ile Leu
                85                  90                  95

Tyr Ile Asp Ala Gly Asn Asn Val Val Tyr Lys Gln Tyr Glu Asp Met
            100                 105                 110

Val Val Glu Ser Cys Gly Cys Arg
        115                 120

<210> SEQ ID NO 4
<211> LENGTH: 84
<212> TYPE: RNA
<213> ORGANISM: Homo sapiens

<400> SEQUENCE: 4
gucagaauaa ugucaaagug cuuacagugc agguagugau augugcaucu acugcaguga      60
aggcacuugu agcauuaugg ugac                                            84

<210> SEQ ID NO 5
<211> LENGTH: 23
<212> TYPE: RNA
<213> ORGANISM: Homo sapiens

<400> SEQUENCE: 5
caaagugcuu acagugcagg uag                                             23
```

```
<210> SEQ ID NO 6
<211> LENGTH: 22
<212> TYPE: RNA
<213> ORGANISM: Homo sapiens

<400> SEQUENCE: 6
acugcaguga aggcacuugu ag                                              22

<210> SEQ ID NO 7
<211> LENGTH: 71
<212> TYPE: RNA
<213> ORGANISM: Homo sapiens

<400> SEQUENCE: 7
guagcacuaa agugcuuaua gugcagguag uguuuaguua ucuacugcau uaugagcacu     60
uaaaguacug c                                                          71

<210> SEQ ID NO 8
<211> LENGTH: 23
<212> TYPE: RNA
<213> ORGANISM: Homo sapiens

<400> SEQUENCE: 8
uaaagugcuu auagugcagg uag                                             23

<210> SEQ ID NO 9
<211> LENGTH: 22
<212> TYPE: RNA
<213> ORGANISM: Homo sapiens

<400> SEQUENCE: 9
acugcauuau gagcacuuaa ag                                              22

<210> SEQ ID NO 10
<211> LENGTH: 82
<212> TYPE: RNA
<213> ORGANISM: Homo sapiens

<400> SEQUENCE: 10
ccugccgggg cuaaagugcu gacagugcag auaguggucc ucccgugcu accgcacugu      60 ggguacuugc ugcuccagca gg                                              82

<210> SEQ ID NO 11
<211> LENGTH: 21
<212> TYPE: RNA
<213> ORGANISM: Homo sapiens

<400> SEQUENCE: 11
uaaagugcug acagugcaga u                                               21

<210> SEQ ID NO 12
<211> LENGTH: 22
<212> TYPE: RNA
<213> ORGANISM: Homo sapiens

<400> SEQUENCE: 12
ccgcacugug gguacuugcu gc                                              22

<210> SEQ ID NO 13
<211> LENGTH: 80
<212> TYPE: RNA
<213> ORGANISM: Homo sapiens
```

```
<400> SEQUENCE: 13 cuggggggcuc caaagugcug uucgugcagg uagugugauu acccaaccua cugcugagcu    60
agcacuuccc gagcccccgg                                                 80

<210> SEQ ID NO 14
<211> LENGTH: 22
<212> TYPE: RNA
<213> ORGANISM: Homo sapiens

<400> SEQUENCE: 14
aaagugcugu ucgugcaggu ag                                              22

<210> SEQ ID NO 15
<211> LENGTH: 22
<212> TYPE: RNA
<213> ORGANISM: Homo sapiens

<400> SEQUENCE: 15
acugcugagc uagcacuucc cg                                              22

<210> SEQ ID NO 16
<211> LENGTH: 81
<212> TYPE: RNA
<213> ORGANISM: Homo sapiens

<400> SEQUENCE: 16
ccuuggccau guaaaagugc uuacagugca gguagcuuuu ugagaucuac ugcaauguaa    60
gcacuucuua cauuaccaug g                                               81

<210> SEQ ID NO 17
<211> LENGTH: 23
<212> TYPE: RNA
<213> ORGANISM: Homo sapiens

<400> SEQUENCE: 17
aaaagugcuu acagugcagg uag                                             23

<210> SEQ ID NO 18
<211> LENGTH: 22
<212> TYPE: RNA
<213> ORGANISM: Homo sapiens

<400> SEQUENCE: 18
cugcaaugua agcacuucuu ac                                              22

<210> SEQ ID NO 19
<211> LENGTH: 69
<212> TYPE: RNA
<213> ORGANISM: Homo sapiens

<400> SEQUENCE: 19
aguaccaaag ugcucauagu gcagguaguu uuggcaugac cuacuguag uaugggcacu     60 uccaguacu                                                             69

<210> SEQ ID NO 20
<211> LENGTH: 23
<212> TYPE: RNA
<213> ORGANISM: Homo sapiens

<400> SEQUENCE: 20
caaagugcuc auagugcagg uag                                             23
```

```
<210> SEQ ID NO 21
<211> LENGTH: 22
<212> TYPE: RNA
<213> ORGANISM: Homo sapiens

<400> SEQUENCE: 21
acuguaguau gggcacuucc ag                                            22

<210> SEQ ID NO 22
<211> LENGTH: 46
<212> TYPE: DNA
<213> ORGANISM: Artificial Sequence
<220> FEATURE:
<223> OTHER INFORMATION: control shRNA template

<400> SEQUENCE: 22
ggatacagat agcagataca agagattgta tctgctatct gtatcc                  46

<210> SEQ ID NO 23
<211> LENGTH: 46
<212> TYPE: DNA
<213> ORGANISM: Artificial Sequence
<220> FEATURE:
<223> OTHER INFORMATION: shGdf6-1

<400> SEQUENCE: 23
gcgcagagct aaggctttat cgagagataa agccttagct ctgcgc                  46

<210> SEQ ID NO 24
<211> LENGTH: 46
<212> TYPE: DNA
<213> ORGANISM: Artificial Sequence
<220> FEATURE:
<223> OTHER INFORMATION: shGdf6-2

<400> SEQUENCE: 24
gcagctcttc ccttgtttat cgagagataa acaagggaag agctgc                  46

<210> SEQ ID NO 25
<211> LENGTH: 46
<212> TYPE: DNA
<213> ORGANISM: Artificial Sequence
<220> FEATURE:
<223> OTHER INFORMATION: shGdf6-3

<400> SEQUENCE: 25
gcaataatgt agtctacaag cgagagcttg tagactacat tattgc                  46
```